(12) United States Patent
Yamaya

(10) Patent No.: US 11,324,391 B2
(45) Date of Patent: May 10, 2022

(54) DISTAL-END COVER FOR ENDOSCOPE, AND ENDOSCOPE

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 287 days.

(21) Appl. No.: 16/585,093

(22) Filed: Sep. 27, 2019

(65) Prior Publication Data

US 2020/0037860 A1 Feb. 6, 2020

Related U.S. Application Data

(63) Continuation of application No. PCT/JP2018/007021, filed on Feb. 26, 2018.

(30) Foreign Application Priority Data

Mar. 30, 2017 (JP) .............................. JP2017-067480

(51) Int. Cl.
*A61B 1/00* (2006.01)
*A61B 1/018* (2006.01)

(52) U.S. Cl.
CPC ...... *A61B 1/00135* (2013.01); *A61B 1/00098* (2013.01); *A61B 1/00101* (2013.01); *A61B 1/00128* (2013.01); *A61B 1/018* (2013.01)

(58) Field of Classification Search
None
See application file for complete search history.

(56) References Cited

U.S. PATENT DOCUMENTS 5,662,588 A * 9/1997 Iida .................... A61B 1/00091
600/121
5,865,726 A * 2/1999 Katsurada ............... A61B 1/12
600/127

(Continued)

FOREIGN PATENT DOCUMENTS

JP H06-315457 A 11/1994
JP 2004-141315 A 5/2004

(Continued)

OTHER PUBLICATIONS

English translation of International Preliminary Report on Patentability dated Oct. 10, 2019, together with the Written Opinion received in related International Application No. PCT/JP2018/007021.

(Continued)

*Primary Examiner* — Timothy J Neal
(74) *Attorney, Agent, or Firm* — Scully, Scott, Murphy & Presser, P.C.

(57) ABSTRACT

A distal-end cover is attached to a distal frame portion of an insertion portion of an endoscope main body, along a longitudinal axis of the insertion portion. The distal-end cover includes a cover main body attached to the distal frame portion and a wall provided on the cover main body. The wall is provided between a tube and a raising portion closer to the distal-end side along the longitudinal axis than a first opening edge portion of the distal frame portion when the cover main body is attached to an outside of the distal frame portion along the longitudinal axis of the insertion portion. The wall is deformed by the tube and an elongated member when the cover main body is removed from the outside of the distal frame portion.

20 Claims, 26 Drawing Sheets

(56) References Cited

U.S. PATENT DOCUMENTS

| | | | | |
|---|---|---|---|---|
| 5,868,663 A | * | 2/1999 | Katsurada | A61B 1/018 600/107 |
| 2004/0082836 A1 | | 4/2004 | Hino | |

FOREIGN PATENT DOCUMENTS

| | | |
|---|---|---|
| JP | 2018-47030 A | 3/2018 |
| WO | WO 2016/027574 A1 | 2/2016 |
| WO | WO 2017/002587 A1 | 1/2017 |
| WO | WO 2017/006705 A1 | 1/2017 |

OTHER PUBLICATIONS

International Search Report dated May 22, 2018 issued in PCT/JP2018/007021.

* cited by examiner

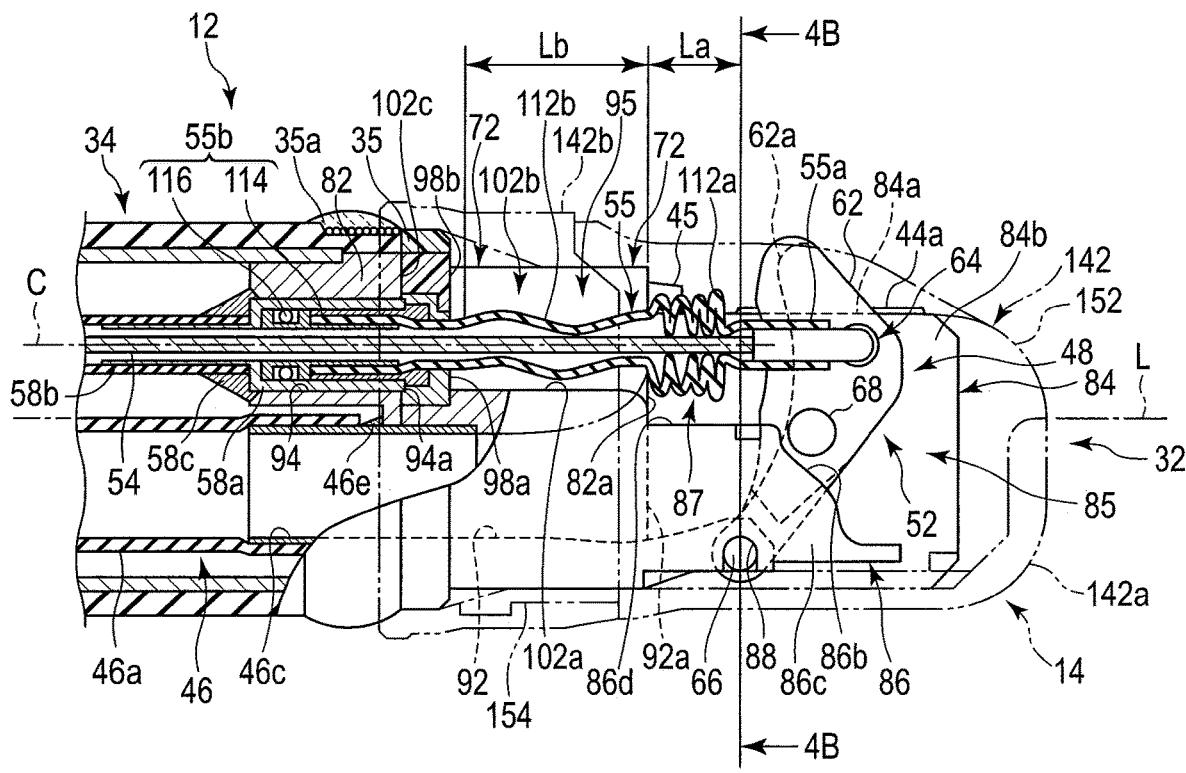
F I G. 4A
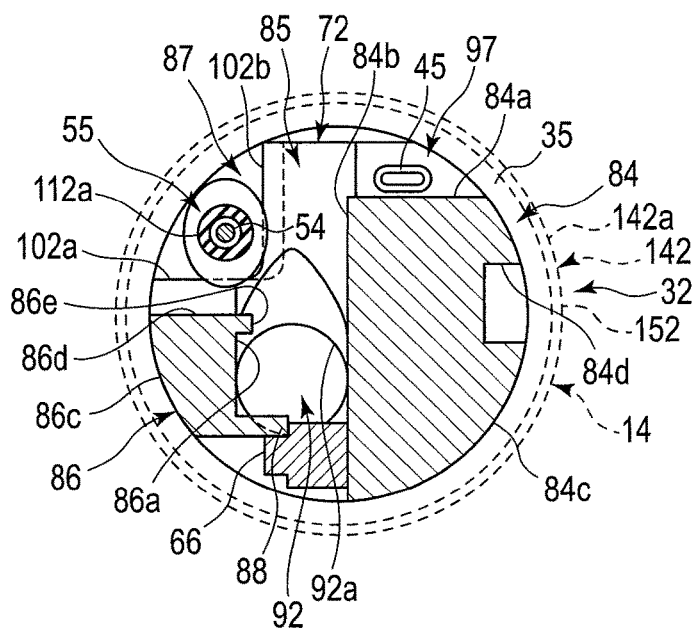
F I G. 4B

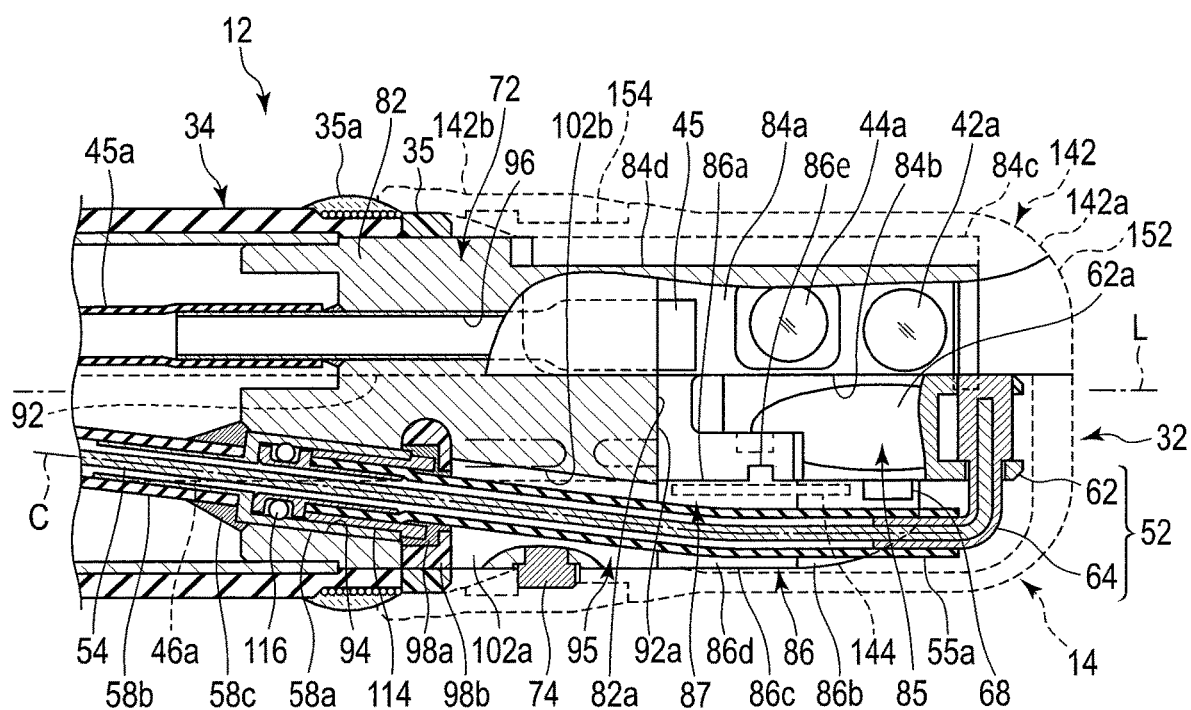
F I G. 5

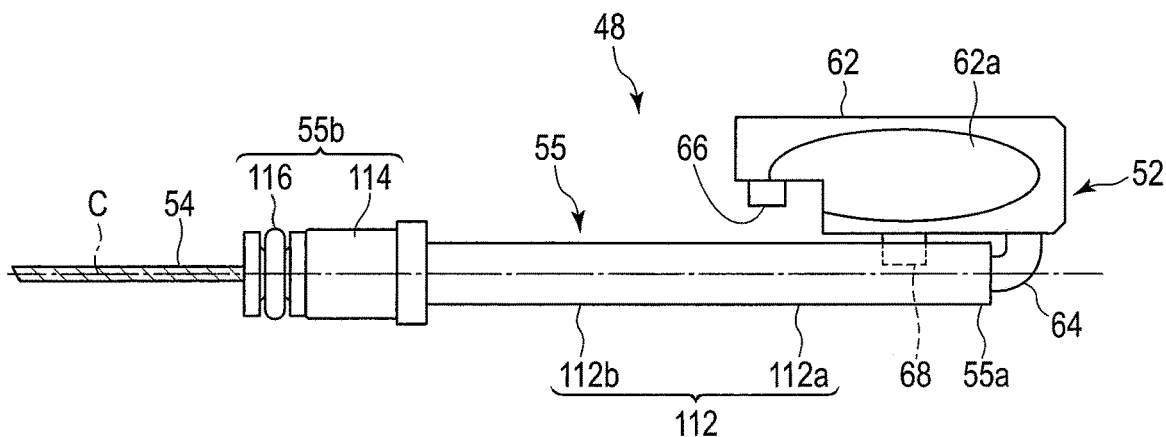
F I G. 6A
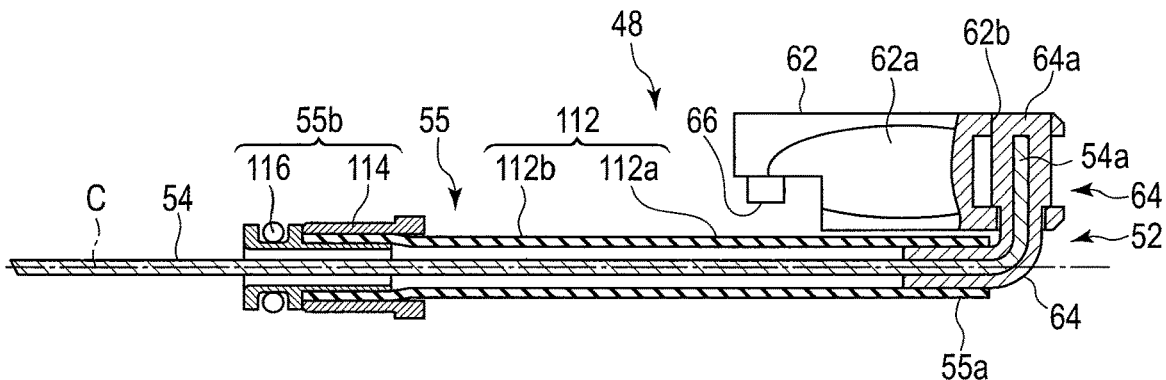
F I G. 6B
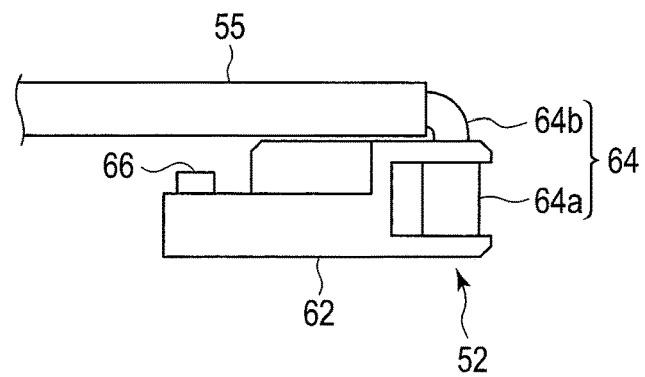
F I G. 6C

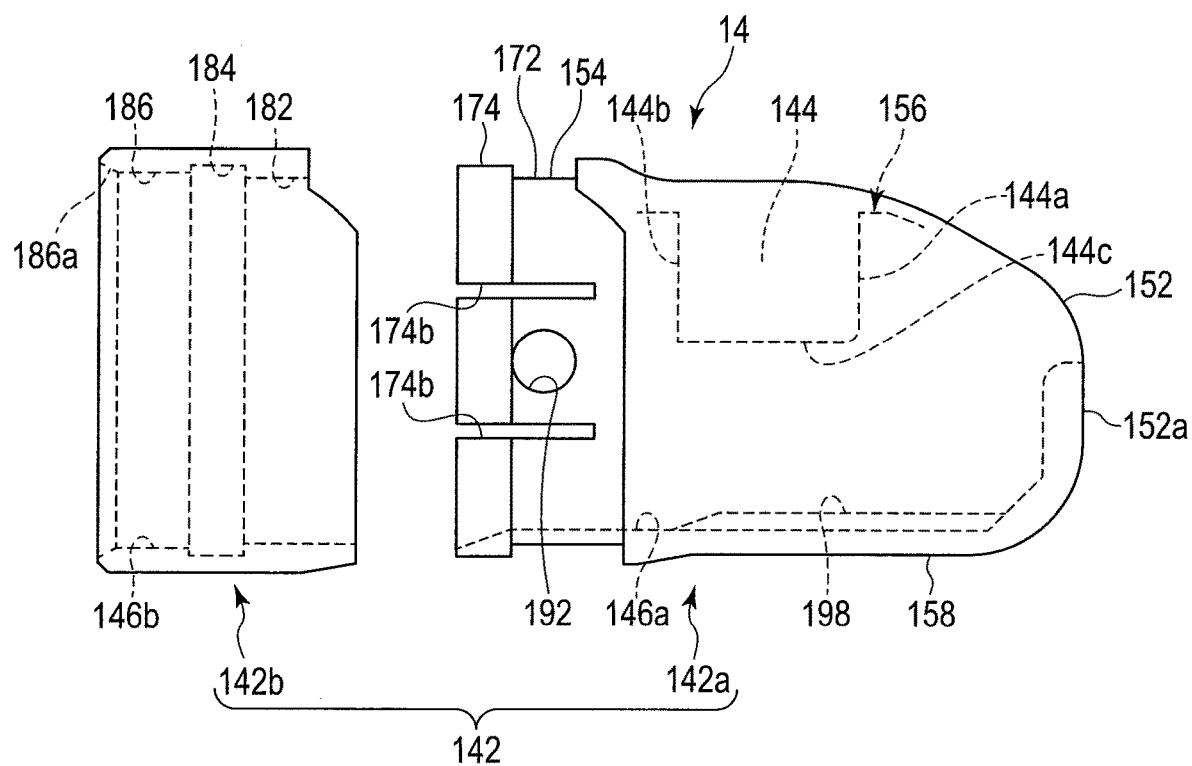
F I G. 7C

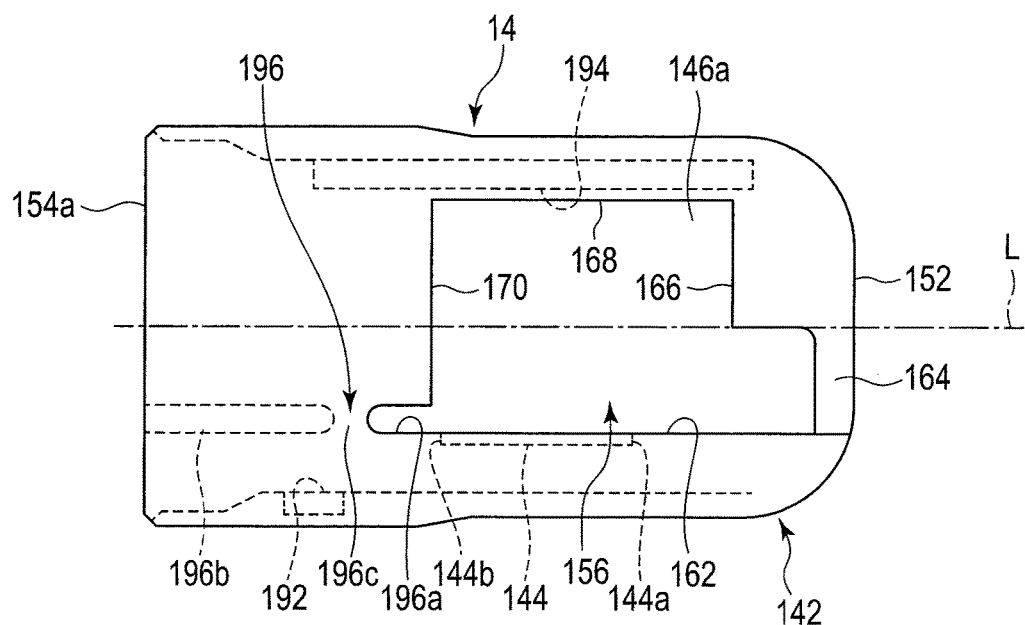
F I G. 16A
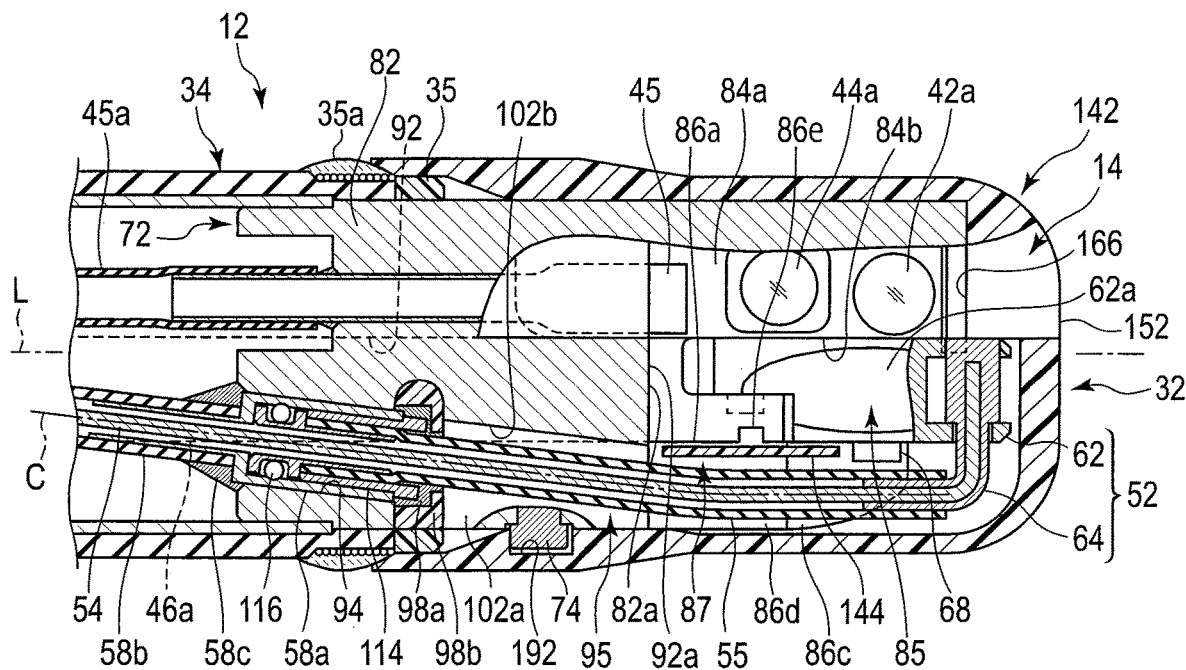
F I G. 16B

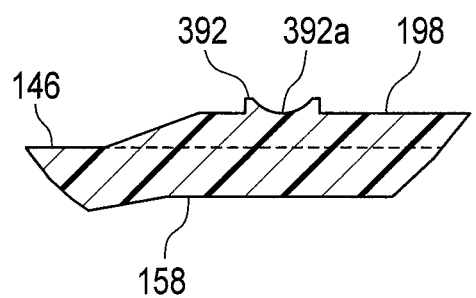
F I G. 26B
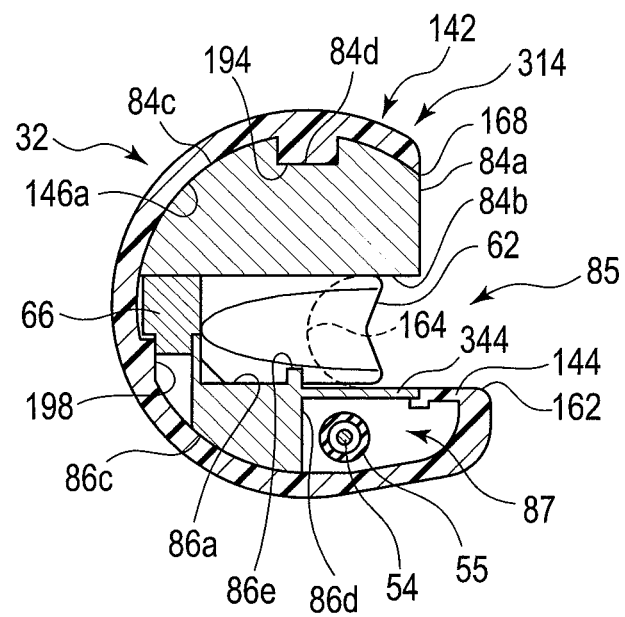
F I G. 27

DISTAL-END COVER FOR ENDOSCOPE, AND ENDOSCOPE

CROSS-REFERENCE TO RELATED APPLICATIONS

This application is a Continuation Application of PCT Application No. PCT/JP2018/007021, filed Feb. 26, 2018 and based upon and claiming the benefit of priority from prior Japanese Patent Application No. 2017-067480, filed Mar. 30, 2017, the entire contents of all of which are incorporated herein by reference.

BACKGROUND OF THE INVENTION

1. Field of the Invention

This invention relates to a distal-end cover for endoscopes, and an endoscope.

2. Description of the Related Art

For example, Jpn. Pat. Appln. KOKAI Publication No. H06-315457 discloses an endoscope. The endoscope includes, on the distal end side of a channel through which an insertion tool such as a treatment instrument is inserted, a mechanism that is configured to change the direction of the distal end of the treatment instrument from a direction along the longitudinal axis of the insertion portion as needed. When a pulling member (elongated member) is moved in the axial direction by operating the raising portion of the endoscope, the raising portion coupled to the distal end of the pulling member disposed on the distal end portion of the insertion portion operates as appropriate around the axis of the support shaft as the pulling member moves.

BRIEF SUMMARY OF THE INVENTION

According to one aspect of the present disclosure, there is provide a distal-end cover for an endoscope, attached to a distal frame portion of an insertion portion of an endoscope main body, which is to be inserted into a subject, along a longitudinal axis of the insertion portion. The distal-end cover includes: a cover main body attached to the distal frame portion; and a wall provided on the cover main body. The wall is provided between a tube and a raising portion provided on the endoscope main body, the wall being closer to the distal-end side along the longitudinal axis than a first opening edge portion of the distal frame portion forming part of a channel through which a treatment instrument is inserted when the cover main body is attached to an outside of the distal frame portion along the longitudinal axis of the insertion portion. The wall is deformed by the tube and an elongated member of the endoscope main body when the cover main body is removed from the outside of the distal frame portion. Where, the elongated member is disposed inside the tube, the elongated member is inserted through a second opening edge portion provided separately from the first opening edge portion, the elongated member is connected to the raising portion, and is configured to be moved along the longitudinal axis of the insertion portion to rotate the raising portion, one end of the tube is watertightly connected to one of the raising portion and the elongated member, and the other end of the tube is watertightly connected to the second opening edge portion, and the raising portion of the endoscope main body is rotatably attached to the distal frame portion, and is configured to raise the treatment instrument to protrude from the first opening edge portion.

Advantage of the invention will be set in the description of the follow, and in part will be obvious from the description or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constituent a part of the specification, illustrate embodiments of the invention, and together with the general description given above and the detailed description of the embodiments given below, serve to explain the principles.

FIG. 4A is a schematic partial sectional view showing a state in which the raising base of the distal-end portion of the insertion portion of the endoscope main body of the endoscope according to the first embodiment is disposed in a raised position.

FIG. 4B is a schematic sectional view taken along line 4B-4B in FIG. 4A.

FIG. 5 is a schematic partial sectional view different from that of FIG. 3A, showing a state in which the raising base of the distal-end portion of the insertion portion of the endoscope main body of the endoscope according to the first embodiment is disposed in a lowered position.

FIG. 6A is a schematic view showing a raising portion of the raising mechanism, a tube and a pulling member (elongated member) through which the tube is inserted with the distal end of the pulling member fixed to the coupling portion of the raising portion, which are disposed in the distal frame portion of the insertion portion of the endoscope main body of the endoscope according to the first embodiment.

FIG. 6B is a schematic view showing a partial section of the raising base of the raising mechanism and sections of the tube and the pulling member, which are shown in FIG. 6A.

FIG. 6C is a schematic view showing the raising portion shown in FIGS. 6A and 6B from the back of FIG. 6A.

FIG. 7C is a schematic view showing the distal-end cover from the direction of arrow 7C in FIG. 7A.

FIG. 16A is a schematic view showing a distal-end cover according to a fifth modification to the first embodiment, which is disposed at the distal-end portion of the insertion portion of the endoscope main body.

FIG. 16B is a schematic partial sectional view showing a state in which the distal-end cover shown in FIG. 16A is attached to the distal-end portion of the insertion portion of the endoscope main body.

FIG. 26B is an enlarged sectional view of the position indicated by symbol 26B in FIG. 26A.

FIG. 27 is a schematic sectional view showing a state in which the distal-end cover according to the first embodiment is attached to the distal-end portion of the endoscope main body according to the second embodiment.

DETAILED DESCRIPTION

Embodiments for carrying out the invention will be described below with reference to the drawings.

First Embodiment

A first embodiment will be described with reference to FIGS. 1 to 11.

Figure 1:
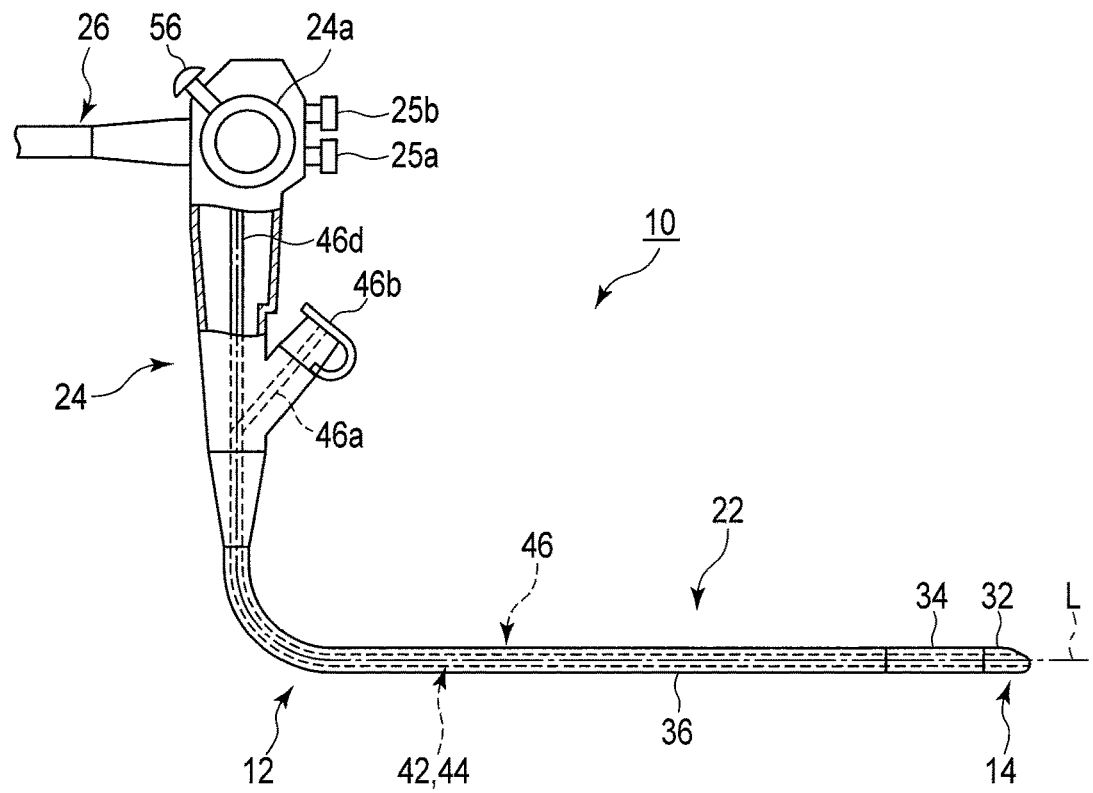
FIG. 1 is a schematic view showing an endoscope according to first and second embodiments each including a modification.

As shown in FIG. 1, an endoscope 10 according to the embodiment includes an endoscope main body 12 and a distal-end cover 14. In the present embodiment, the cover 14 is described mainly as being formed as a disposable type. If the cover 14 is attached to the endoscope main body 12 and so formed that it can be cleaned, disinfected and sterilized as appropriate, the attachment to the endoscope main body 12 may be maintained. Thus, the cover 14 described here is not limited to a disposable type.

The endoscope main body 12 includes an insertion portion 22 to be inserted into a subject, an operation portion 24 provided at the proximal end of the insertion portion 22 and grasped by a user, and a universal cord 26 extending from the operation portion 24. The distal-end cover 14 is attached to the distal end of the insertion portion 22 along its longitudinal axis L.

The longitudinal axis L of the insertion portion 22 is defined by the distal end and the proximal end of the insertion portion 22. The insertion portion 22 includes a distal-end portion 32 (see FIG. 2), a bending portion 34 and a tube portion 36, which are arranged in order from the distal end to the proximal end. The foregoing distal-end cover 14 is attached to the distal-end portion 32 to cover part of the outer circumferential surface of the distal-end portion 32.

The tube portion 36 may be what is called a flexible scope having flexibility or what is called a rigid scope that maintains its straight state and has resistance to bending. The bending portion 34 can be bent in a plurality of directions such as two or four directions by operating a knob 24a of the operation portion 24 using a known mechanism. When a lever (raising state adjustment portion) 56 is operated, a pulling member 54 to be described later moves along the longitudinal axis L of the insertion portion 22. Accordingly, a raising portion 52 to be described later rotates relative to a distal frame portion 72 of the insertion portion 22. The raising portion 52 can be moved between a lowered position (initial position) shown in FIG. 3A and a maximum raised position shown in FIG. 4A. The raising portion 52 is usually located in the lowered position shown in FIG. 3A.

As shown in FIGS. 2, 3A, 4A and 5, an annular electrical insulating member 35 is fixed to the distal end of the bending portion 34. The insulating member 35 is disposed on the outer circumferential surface of a block-shaped distal frame portion 72 to be described later. A thread wound portion 35a is formed at a position adjacent to the proximal end side of the insulating member 35.

As shown in FIG. 1, the endoscope main body 12 includes an illumination optical system 42, an observation optical system 44 and a treatment instrument insertion channel 46. In addition, the endoscope main body 12 includes an air-supply/water-supply mechanism and a suction mechanism (not shown). The air-supply/water-supply mechanism includes a nozzle 45 and a tube 45a (see FIG. 5), which are to be described later, on its distal end and is operated by a button 25a of the operation portion 24 shown in FIG. 1. The suction mechanism communicates with the channel 46 and is operated by a button 25b of the operation portion 24 shown in FIG. 1.

Figure 2:
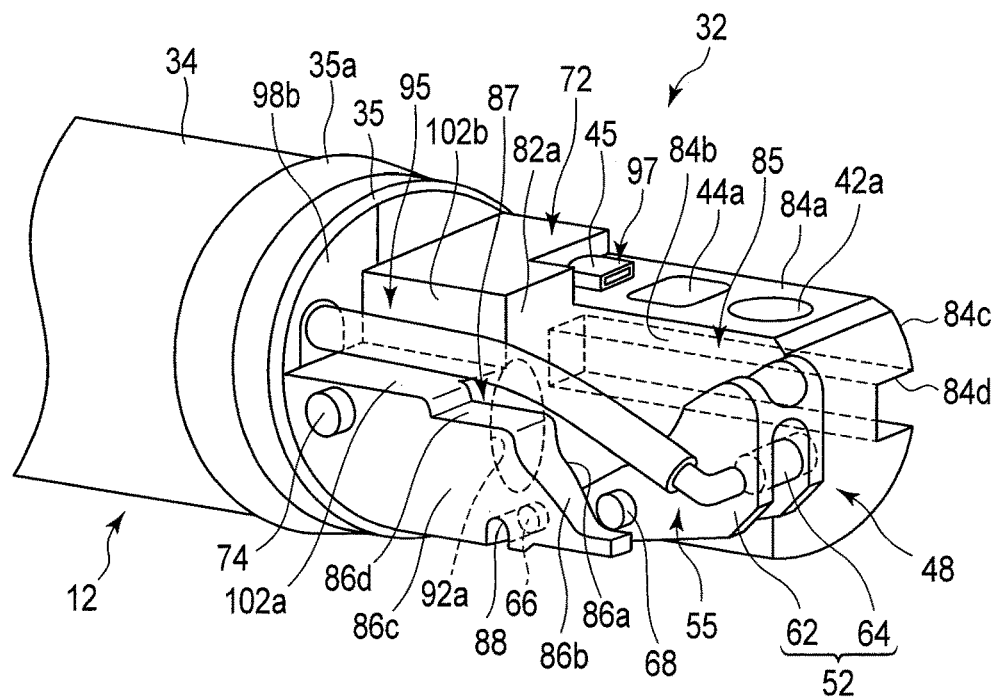
FIG. 2 is a schematic perspective view showing a distal-end portion and a bending portion of the insertion portion of the endoscope main body of the endoscope according to the first embodiment.

The illumination optical system 42 and the observation optical system 44 are disposed inward from the distal-end portion 32, bending portion 34, tube portion 36, operation portion 24 and universal cord 26 of the insertion portion 22 of the endoscope main body 12. As shown in FIG. 2, the illumination optical system 42 includes an illumination window 42a on the distal-end portion 32. The observation optical system 44 includes an observation window 44a on the distal-end portion 32. The following is a description of a case where the observation optical system 44 is formed as a side-viewing type for observation in a direction orthogonal to the longitudinal axis L. However, it may be formed as an oblique-viewing type for observation in a direction away from the longitudinal axis L. The side-viewing type and oblique-viewing type observation optical systems 44 are each known. The endoscope main body 12 including the side-viewing type observation optical system 44 will be described below.

Figure 3A:
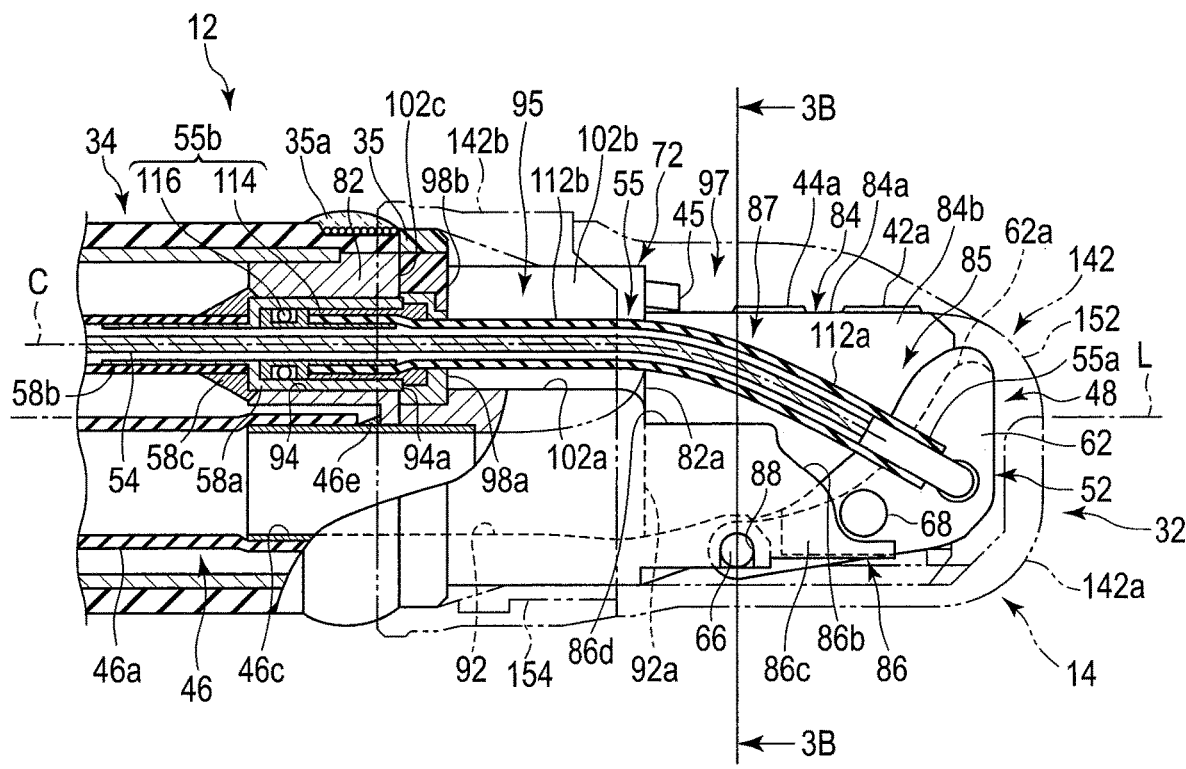
FIG. 3A is a schematic partial sectional view showing a state in which the raising base of the distal-end portion of the insertion portion of the endoscope main body of the endoscope according to the first embodiment is disposed in a lowered position.

As shown in FIGS. 2, 3A, 4A and 5, the distal end of the channel 46 is opened in the distal frame portion 72 of the insertion portion 22 of the endoscope main body 12. As shown in FIG. 1, the proximal end of the channel 46 is opened near the proximal-end portion of the tube portion 36 of the insertion portion 22 or in the operation portion 24. In this case, as shown in FIG. 1, the proximal end of the channel 46 has an opening (not shown) in the operation portion 24, and a forceps plug 46b is detachable to the opening through a mouth ring (not shown). As shown in FIGS. 3A, 4A and 5, the distal end of a tube 46a of the channel 46 is fixed to the distal frame portion 72 through a mouth ring 46c. Note that the tube 46a of the channel 46 branches to a known suction path 46d inside, for example, the operation portion 14. The suction path 46d is coupled to the button 25b. Pressing the button 25b will discharge sucked substances from a distal-end opening 92a (to be described later) of the distal end of the channel 46 through the mouth ring 46c, tube 46a, suction path 46d and universal cord 26.

As described above, in this embodiment, the distal-end portion 32 is formed as a side-viewing type with a different observation direction relative to a direction along the longitudinal axis L of the insertion portion 22. As shown in FIGS. 2 to 6c, the endoscope main body 12 includes a raising mechanism 48 that can properly adjust the direction of a treatment instrument (not shown) or the like inserted into the channel 46 at the distal-end portion 32 so as to set the treatment instrument in the visual field of the observation optical system 44.

The distal end of the raising mechanism 48 is located in the distal-end portion 32 of the insertion portion 22 of the endoscope main body 12, and the proximal end thereof is located in the operation portion 24 (see FIG. 1). The raising mechanism 48 includes a raising portion 52 supported by the distal frame portion 72, an elongated member (to be referred to as a pulling member hereinafter) 54 (see FIG. 3A, etc.) that moves in the axial direction to actuate the raising portion 52, and the lever 56 (see FIG. 1) supported by the operation portion 24.

The raising portion 52 is provided on the distal-end portion 32 of the insertion portion 22. The raising portion 52 is rotatably attached to the distal frame portion 72. The raising portion 52 is provided on the distal-end side of the mouth ring 46c and a first cylindrical surface (first opening edge portion) 92 to be described later and the distal-end side of the mouth ring 58a and a second cylindrical surface (second opening edge portion) 94 to be described later to operate relative to the distal frame portion 72. The raising portion 52 can adjust the direction of the distal-end portion of the treatment instrument, such as raising of the treatment instrument projected from the first cylindrical surface 92 of the channel 46.

As the pulling member 54, for example, a wire and a rod-like member (rod) having flexibility are used. The pulling member 54 extends to the proximal-end side of the distal frame portion 72 through the passage (mouth ring 58a) (see FIG. 3A, etc.) of the distal frame portion 72 of the distal-end portion 32 of the insertion portion 22. The pulling member 54 is thus inserted through the second opening edge portion 94 of the distal frame portion 72. The pulling member 54 then extends to the operation portion 24 through the interiors of the bending portion 34 and the tube portion 36. The proximal end (the other end) of the pulling member 54 is connected to the lever 56 of the operation portion 24. The length of the pulling member 54 is adjusted. The distal end (one end) of the pulling member 54 is connected to the raising portion 52. In other words, a distal-end portion 54a of the pulling member 54 on its distal-end side is connected to the raising portion 52. Note that the raising portion 52 is part of the distal-end portion 32. In addition, the distal-end portion 54a of the pulling member 54 and its neighboring portion are also part of the distal-end portion 32.

The raising portion 52 includes a raising base 62 including a guide path 62a for treatment instruments and a coupling portion 64 coupled to the raising base 62. The raising base 62 is formed into an almost triangular prism shape. The raising base 62 is provided with a pivot shaft 66 that is orthogonal to, for example, the longitudinal axis L and also orthogonal to the observation direction and a guide pin 68 that is supported on a guide surface 86b, which is to be described later, to guide the raising base 62 so as to allow it to move in a predetermined range. The raising base 62 is preferably formed integrally with the pivot shaft 66 and the guide pin 68. The raising base 62 rotates on the pivot shaft 66 that is orthogonal to, for example, the longitudinal length L. The raising portion 52 can thus rotate on the pivot shaft 66 relative to the distal frame portion 72. Note that the pivot shaft 66 of the raising base 62 of the raising portion 52 need not always be orthogonal to the longitudinal axis L and is allowed to shift as needed. The axial direction of the pivot shaft 66 of the raising base 62 of the raising portion 52 need not always be orthogonal to the observation direction of the observation optical system 44 and is allowed to shift as needed.

As shown in FIGS. 2 to 5, the distal frame portion 72 is provided on the distal-end side of the insertion portion 22 along the longitudinal axis L. The distal frame portion 72 is formed like a block. The distal frame portion 72 is formed by, for example, cutting a cylindrical column made of a hard material such as a metal like stainless steel or a hard resin. The distal frame portion 72 generally includes an almost columnar base 82 and first and second convex portions 84 and 86 extending from the distal end 82a of the base 82 to the distal-end side along the longitudinal axis L. The outer circumference of the base 82 of the distal frame portion 72 is covered by the distal-end portion of a flexible tube made of rubber on the outermost circumference of the bending portion 34. The thread wound portion 35a brings the distal-end portion of the flexible tube of the bending portion 34 into tight contact with the outer circumference of the base 82 of the distal frame portion 72. The insulating member 35 is disposed at the distal end of the flexible tube of the bending portion 34.

The first convex portion 84 is provided with the illumination window 42a of the illumination optical system 42 and the observation window 44a of the observation optical system 44. The illumination window 42a of the illumination optical system 42 and the observation window 44a of the observation optical system 44 are directed in a direction orthogonal to the longitudinal axis L. The base 82 is provided with the nozzle 45. The nozzle 45 is provided on the proximal-end side of the illumination window 42a of the illumination optical system 42 and the observation window 44a of the observation optical system 44. The opening of the nozzle 45 is directed to the illumination window 42a of the illumination optical system 42 and the observation window 44a of the observation optical system 44. The nozzle 45 can discharge a liquid such as physiological saline toward the observation window 44a and illumination window 42a and blow off deposits on the observation window 44a and illumination window 42a by supplying air.

The first convex portion 84 includes an arrangement surface 84a on which the illumination window 42a of the illumination optical system 42 and the observation window 44a of the observation optical system 44 are arranged, a defining surface (flat surface) 84b that defines the moving direction of the raising base 62, and an outer circumferential surface 84c. The arrangement surface 84a is preferably formed as a surface that extends along the longitudinal axis L and is parallel to the pivot shaft 66 of the raising portion 52. The defining surface 84b is preferably a flat surface that extends along the longitudinal axis L and is orthogonal to the pivot shaft 66 of the raising portion 52. In this case, the defining surface 84b is orthogonal to the arrangement surface 84a. The outer circumferential surface 84c is formed as a curved surface of a cylindrical column.

A concave portion (guide groove) 84d is formed in the outer circumferential surface 84c along the longitudinal axis L. The concave portion 84*d* is formed at a position apart from the raising portion 52 of the raising mechanism 48 and the pulling member 54. Preferably, the concave portion 84*d* is formed continuously from the distal end to the proximal end of the distal frame portion 72. A guide projection portion 194 (to be described later) of the distal-end cover 14 is fit into the concave portion 84*d*. Therefore, the distal-end cover 14 is attached to the distal frame portion 72 in a predetermined state.

The second convex portion 86 includes a defining surface 86*a* that faces the defining surface 84*b* of the first convex portion 84, a guide surface 86*b* that guides the pivotal movement of the raising base 62, an outer circumferential surface 86*c*, and an extension surface 86*d* extending from the base portion 82. Preferably, the defining surface 86*a* of the second convex portion 86 is a flat surface that is separated from the defining surface 84*b* of the first convex portion 84 and is parallel to the defining surface 84*b* of the first convex portion 84. The outer circumferential surface 86*c* is formed as a curved surface of a cylindrical column. A projection 86*e* is formed on the defining surface 86*a* of the second convex portion 86 so as to come into contact with the raising base 62 when the raising base 62 is at the raised position. The projection 86*e* defines the maximum raised position at which the raising base 52 is raised most.

The raising base 62 is disposed between the defining surface 84*b* of the first convex portion 84 and the defining surface 86*a* of the second convex portion 86, and space 85 is also formed therebetween to allow the raising base 62 to operate within a predetermined range. In the space 85, in particular, the raising base 62 is disposed and moved within a predetermined range. A support portion 88 that supports the pivot shaft 66 of the raising base 62 is disposed on the defining surface 84*b* of the first convex portion 84 and the defining surface 86*a* of the second convex portion 86 at positions separated from the arrangement surface 84*a* of the first convex portion 84 and the extension surface 86*d* of the second convex portion 86. The support portion 88 that supports the raising portion 52 operably is thus included in the distal frame portion 72. In this case, the support portion 88 is formed into an almost U shape. The raising base 62 is disposed in the space 85, and the pivot shaft 66 is disposed on the support portion 88. The cover 14 is attached to the outside of the distal frame portion 72 and the raising portion 52. A convex portion 198 of the inner circumferential surface 146 (to be described later) of the cover 14 prevents the pivot shaft 66 of the raising base 62 from slipping off from the support portion 88 of the distal frame portion 72.

The guide pin 68 of the raising base 62 is placed on the guide surface 86*b* of the second convex portion 86 while the raising base 62 is disposed in the space 85 and the pivot shaft 66 is disposed on the support portion 88. The guide surface 86*b* is formed as a proper curved surface to move the guide pin 68 between the position shown in FIGS. 2 to 3B and the position shown in FIGS. 4A and 4B while supporting the guide pin 68 of the raising base 62. The raising portion 52 thus operates on the pivot shaft 66 and the support portion 88 by the pulling force from the pulling member 54.

The maximum width (height) W2 of the defining surface 86*a* of the second convex portion 86 in a direction orthogonal to the longitudinal axis L is, for example, about half of the maximum width (height) W1 of the defining surface 84*b* of the first convex portion 84 in a direction orthogonal to the longitudinal axis L. A movement space 87 which continues with the foregoing space 85 and in which the pulling member 54 and a tube (tubular elastic member) 55 covering the pulling member 54 move, is formed in a region adjacent to one side of the second convex portion 86 to which the extension surface 86*d* is directed.

The base portion 82 of the distal frame portion 72 includes the first cylindrical surface (first opening edge portion) 92 in which a first through-hole (channel hole) through which a treatment instrument extends is formed and the second cylindrical surface (second opening edge portion) 94 in which a second through-hole (a passage for the pulling member 54 of the raising mechanism 48) inclined with respect to, for example, the longitudinal axis L is formed. The distal frame portion 72 thus includes the first opening edge portion 92 that is formed as a distal-end portion (part) of the channel 46 through which a treatment instrument (not shown) is inserted and the second opening edge portion 94 that is provided separately from the first opening edge portion 92. The base portion 82 of the distal frame portion 72 also includes a third cylindrical surface 96 in which a third through-hole (a passage for the nozzle 45) along, for example, the longitudinal axis L is formed. The first, second and third cylindrical surfaces 92, 94 and 96 are each allowed to have an appropriate shape. Preferably, the first and second cylindrical surfaces 92 and 94 are, for example, cylindrical. The inner diameter of the first cylindrical surface 92 is preferably larger than that of the second cylindrical surface 94.

The first cylindrical surface 92 extends through the distal frame portion 72 in parallel to or almost in parallel to, for example, the longitudinal axis L. More specifically, the first cylindrical surface 92 extends through the base portion 82 of the distal frame portion 72. The first cylindrical surface 92 thus extends along, for example, the longitudinal axis L so as to make the distal end side of the base portion 82 of the distal frame portion 72 communicate with the proximal end side thereof. On the distal-end side of the first cylindrical surface 92, the foregoing appropriate space 85 is formed in cooperation with the first and second convex portions 84 and 86 and also the cover 14.

The second cylindrical surface (introduction hole) 94 extends through the distal frame portion 72 so as to be inclined relative to, for example, the longitudinal axis L. More specifically, the second cylindrical surface 94 extends through the base portion 82 of the distal frame portion 72. The second cylindrical surface 94 thus makes the distal-end side of the base portion 82 of the distal frame portion 72 communicate with the proximal-end side thereof. On the distal-end side of the second cylindrical surface 94, an appropriate space 95 is formed in cooperation with the base portion 82 and the cover 14. The space 95 continues with the proximal-end sides of the foregoing space 85 and space 87 along the longitudinal axis L. Since the through-hole direction of the second cylindrical surface 94 is inclined relative to the longitudinal axis L, the length (the length of an elastic member 112 to be described later) between the distal end (one end) 55*a* of the tube 55 and the proximal end (the other end) 55*b* thereof can be maximized in the distal-end portion 32, and the deformation amount of the elastic member 112 per unit volume can be reduced. Depending on the selection of a material for the elastic member 112, the through-hole direction of the second cylindrical surface 94 preferably extends along the longitudinal axis L.

Note that the through-hole direction of the second cylindrical surface 94 coincides or almost coincides with the axial direction of the central axis (longitudinal axis) C of the pulling member 54.

The third cylindrical surface 96 extends though the distal frame portion 72 along, for example, the longitudinal axis L. Specifically, the third cylindrical surface 96 extends through the base portion 82 of the distal frame portion 72. Thus, the third cylindrical surface 96 extends along, for example, the longitudinal axis L so as to make the distal-end side of the base portion 82 of the distal frame portion 72 communicate with the proximal-end side thereof. On the distal-end side of the third cylindrical surface 96, an appropriate space 97 in which the distal end of the nozzle 45 is disposed, is formed in cooperation with the first convex portion 84 and the cover 14.

The first cylindrical surface 92 forms the distal-end opening 92a of the channel 46. The mouth ring 46c is fixed to the first cylindrical surface 92. The channel tube 46a is fixed to the proximal-end portion of the mouth ring 46c.

As described above, the second cylindrical surface 94 is formed so as to be inclined relative to the longitudinal axis L. The pulling member 54 of the raising mechanism 48 extends through the second cylindrical surface 94. The mouth ring (passage) 58a is fixed to the second cylindrical surface 94. The mouth ring 58a forms a through hole (introduction hole) and forms a passage through which the pulling member 54 extends. That is, the distal frame portion 72 includes the mouth ring 58a as a passage that makes the distal-end side communicate with the proximal-end side. A tube 58b is fixed to the proximal-end portion of the mouth ring 58a. For example, an adhesive agent 58c is annularly applied to the proximal end of the second cylindrical surface 94 of the base portion 82 of the distal frame portion 72 and between the mouth ring 58a and the tube 58b. This prevents a fluid (a liquid, gas, etc.) from leaking from the distal end of the mouth ring 58a to the proximal-end side of the mouth ring 58a through between the outer circumferential surface of the mouth ring 58a and the base portion 82.

While the proximal-end portion of the tube 55 is disposed on the second cylindrical surface 94, an adhesive agent 98a and a retaining plate (protective plate) 98b are disposed on the mouth ring 58a. The adhesive agent 98a and retaining plate 98b are preferably disposed inside the insulating member 35. Since the adhesive agent 98a and retaining plate 98b are disposed on the distal end 94a of the second cylindrical surface 94 of the base portion 82, the adhesive agent 98a and retaining plate 98b maintain the proximal-end portion of the tube 55 fit into the mouth ring 58a and prevent it from slipping off from the mouth ring 58a. In addition, the adhesive agent 98a prevents a liquid from infiltrating from the distal-end side into the proximal-end side through between the outer circumferential surface of a mouth ring 114 (to be described later) of the tube 55 and the inner circumferential surface of the mouth ring 58a and between the outer circumferential surface of the mouth ring 58a and the second cylindrical surface 94, that is, between the outer circumferential surface of the mouth ring 114 and the second cylindrical surface 94.

The base portion 82 of the distal frame portion 72 includes a first wall surface 102a, a second wall surface 102b and a third wall surface 102c on the distal-end side of the second cylindrical surface 94. The first wall surface (bottom surface) 102a, second wall surface (side surface) 102b and third wall surface (proximal-end surface) 102c are formed at positions closer to the proximal-end side than the distal-end opening 92a of the first cylindrical surface (channel hole) 92 along the longitudinal axis L. The first wall surface 102a, second wall surface 102b and third wall surface 102c form the space (gap) 95 between an opening edge 156 (to be described later) and/or the inner circumferential surface 146 of the cover 14. In the present embodiment, the first wall surface 102a is formed parallel to the arrangement surface 84a of the first convex portion 84 and the extension surface 86d of the second convex portion 86. The first wall surface 102a is located between the arrangement surface 84a of the first convex portion 84 and the extension surface 86d of the second convex portion 86 in a direction orthogonal to the longitudinal axis L.

The nozzle 45 extends through the third cylindrical surface 96 and is fixed thereto. The tube 45a is fixed to the proximal end of the nozzle 45.

The distal end (distal-end opening) 92a of the first cylindrical surface 92 is formed closer to the distal-end side, along the longitudinal axis L, than the distal end 94a of the second cylindrical surface 94. The distal end 92a of the first cylindrical surface 92 is formed on the proximal-end side of the raising base 62. The distal end 92a of the first cylindrical surface 92 is formed along the longitudinal axis L so as to be closer to the distal-end side than the distal end 94a of the second cylindrical surface 94. Thus, in the distal frame portion 72, the length of the elastic member 112 (to be described later) of the tube 55 can be maximized, and the deformation amount of the elastic member 112 per unit volume can be reduced when the elastic member 112 is compressed along a central axis C.

An engaging pin 74 is fixed on the outer circumferential surface of the base portion 82 of the distal frame portion 72. Preferably, the pin 74 is adjacent to the space 95 (first wall surface 102a) in the circumferential direction of the longitudinal axis L and is formed almost opposed to the concave portion (guide groove) 84d with the longitudinal axis L of the distal frame portion 72 therebetween.

As shown in FIG. 6B, the raising base 62 of the raising portion 52 includes a fitting portion 62b in which the coupling portion 64 is fit. The fitting portion 62b of the raising base 62 is formed into a concave portion or a through hole in which the coupling portion 64 is disposed. In this case, the fitting portion 62b extends through the raising base 62 in a direction orthogonal to the longitudinal axis L.

The coupling portion 64 can rotate relative to the raising base 62 as appropriate as shown in FIGS. 3A and 4A, while the distal-end portion 54a of the pulling member 54 is fixed to a cylindrical body 64a.

The outer circumference of the pulling member 54 is covered with the cylindrical tube 55. The pulling member 54 is thus disposed inside the tube 55. The central axis of the cylindrical tube 55 coincides or almost coincides with the central axis C of the pulling member 54. The tube 55 includes the expandable cylindrical elastic member 112 that is elastically deformed along the axial direction of the pulling member 54, the mouth ring 114 fixed to the proximal end (the other end) of the elastic member 112, and an O-shaped ring 116 disposed on the outer circumference of the mouth ring 114.

In the present embodiment, the distal end (one end) 55a of the elastic member 112 of the tube 55 is fixed to a tubular body 64b of the coupling portion 64 by, for example, adhesive bonding. The inner circumferential surface of the distal end 55a of the elastic member 112 is entirely in tight contact with the outer circumferential surface of the tubular body 64b of the coupling portion 64. This prevents a liquid and gas from infiltrating the interior of the elastic member 112 from the distal end (one end) 55a of the elastic member 112 of the tube 55. That is, the one end 55a of the tube 55 is watertightly connected to the raising portion 52.

As shown in FIGS. 6A and 6B, the other end 55b of the tube 55 is formed by the elastic member 112, the mouth ring 114 and the O-shaped ring 116. The mouth ring 114 fixes the proximal end of the elastic member 112 by, for example, clamping. The mouth ring 114 may be formed integrally or formed from a plurality of members such as two members. The O-shaped ring 116 prevents a liquid from moving from between the outer circumferential surface of the mouth ring 114 and the inner circumferential surface of the O-shaped ring 116 along the axial direction of the mouth ring 114.

The proximal end (the other end) 55b of the tube 55 is fit on the inner circumferential surface (annular circumferential surface) of the mouth ring 58a fixed to the distal frame portion 72. It is preferable that the inner diameter of the mouth ring 58a be slightly larger than the outer diameter of the mouth ring 114 of the other end 55b of the tube 55 and be slightly smaller than the outer diameter of the O-shaped ring 116. That is, the other end 55b of the tube 55 is watertightly connected to the distal frame portion 72 via the mouth ring 58a. Thus, the other end 55b of the tube 55 has a structure that doubly prevents a liquid from infiltrating the proximal-end side from the distal-end side through the passage (through hole) 58a with the adhesive agent 98a and the O-shaped ring 116. Therefore, the other end (proximal end) 55b of the tube 55 is watertightly connected to the second opening edge portion 94 of the distal frame portion 72.

As shown in FIG. 5, while the proximal end (the other end) 55b of the tube 55 is fit to the inner circumferential surface of the mouth ring 58a, the adhesive agent 98a and the retaining plate 98b are disposed on the base portion 82. This maintains the state of fitting the other end 55b of the tube 55 into the mouth ring 58a even if a force is added to release the state of fitting the other end 55b of the tube 55 into the mouth ring 58a during the use of the endoscope main body 12. Note that the length of a portion of the elastic member 112, which protrudes from the retaining plate 98b toward the distal end (the effective length of the deformable portion of the elastic member 112 excluding one end 55a and the other end 55b) is preferably, for example, about 20 mm.

The elastic member 112 of the tube 55 shown in FIGS. 6A and 6B is formed of a resin material that can be deformed as the pulling member 54 is pulled. The entire portion of the elastic member 112 between one end 55a and the other end 55b, in particular, is preferably deformable. The elastic member 112 includes a distal-end side region 112a and a proximal-end side region 112b. In the present embodiment, the proximal end of the distal-end side region 112a is continuous with the distal end of the proximal-end side region 112b. As described above, when the portion of the elastic member 112 which protrudes from the retaining plate 98b toward the distal end has a length of about 20 mm, the distal-end side region 112a and the proximal-end side region 112b each preferably have a length of, for example, about 10 mm. In addition, in the present embodiment, the elastic member 112 has a constant thickness from the distal end to the proximal end. On the other hand, the distal-end side region 112a and the proximal-end side region 112b of the elastic member 112 may be formed of different materials and each may have deformability adjusted by composition adjustment. The distal-end side region 112a of the elastic member 112, which is close to the one end 55a, has a property of being more deformable than the proximal-end side region 112b, which is close to the other end 55b. For example, the undeformability of the proximal-end side region 112b is preferably higher by 10% to 30%, preferably 20%, than that of the distal-end side region 112a. For example, the distal-end side region 112a of the elastic member 112 is preferably formed of a fluorine resin or silicone resin, whereas the proximal-end side region 112b is preferably formed of an urethane resin. In addition, for example, the proximal-end side region 112b of the elastic member 112 and the boundary between the proximal-end side region 112b and the distal-end side region 112a may be formed by two-color molding (different material molding) using the above resin materials as needed. Resin materials are properly selected for the elastic member 112 so as to maintain the deformability of the distal-end side region 112a higher than that of the proximal-end side region 112b when a compression force is exerted along the central axis C.

In this manner, the elastic member 112 is formed such that the distal-end side region 112a located close to the one end 55a is more deformable upon compression along the central axis C of the tube 55 with respect to the proximal-end side region 112b located close to the other end 55b. Accordingly, when the elastic member 112 is compressed along the central axis C, the reduction ratio of the length of the distal-end side region 112a as compared with the length before compression is higher than that of the proximal-end side region 112b. That is, the side of the elastic member 112 which is connected to the raising portion 52 is more deformable than the side of the elastic member 112 which is connected to the periphery of the through hole.

The distal-end side region 112a of the elastic member 112 is preferably provided with a creasing tendency in advance so as to form a plurality of creases when being compressively deformed along the axial direction of the elastic member 112 as shown in FIG. 4A. For example, when the distal-end side region 112a is compressively deformed along the axial direction of the elastic member 112, a plurality of creases (a plurality of ridges and valleys) are preferably formed. Assume that when the distal-end side region 112a of the elastic member 112 is compressively deformed along the axial direction of the elastic member 112, only one ridge is formed. In this case, the distal-end side region 112a can have a large maximum outer diameter. In contrast to this, forming a plurality of creases, that is, a plurality of ridges together with a plurality of valleys instead of only one ridge, can reduce the maximum outer diameter of the distal-end side region 112a. Assume that in the following description, when the distal-end side region 112a of the elastic member 112 is compressively deformed along the axial direction of the elastic member 112, a plurality of creases are formed.

Figure 3B:
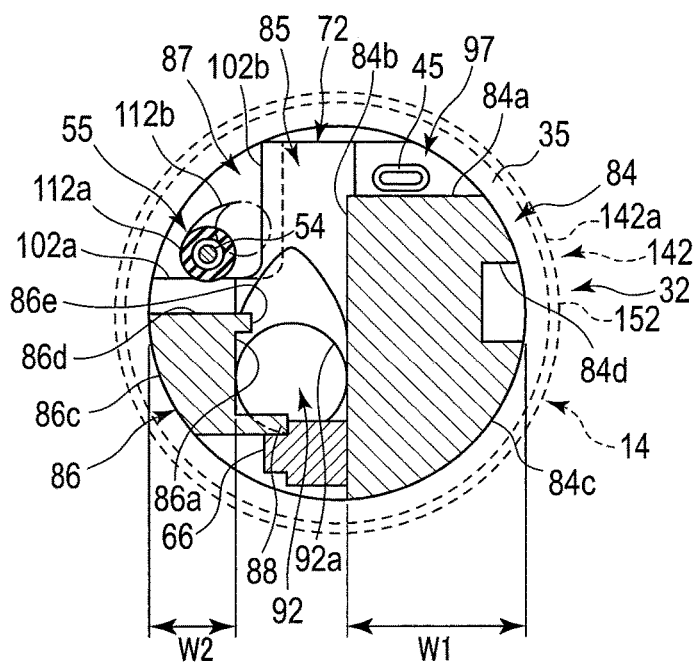
FIG. 3B is a schematic sectional view taken along line 3B-3B in FIG. 3A.

As shown in FIGS. 3A and 3B, when the elastic member 112 of the tube 55 has a natural length, the distal-end side region 112a can be disposed in the space 85 and the space 87, and the proximal-end side region 112b can be disposed in the space 87 and the space 95. Accordingly, the distal-end side region 112a of the elastic member 112 of the tube 55 is disposed between the distal-end opening 92a of the first cylindrical surface 92 and the raising portion 52 along the longitudinal axis L. In addition, it is preferable that only the proximal-end side region 112b of the elastic member 112 be disposed, without the distal-end side region 112a, between the distal end 94a of the passage 94 and the distal-end opening 92a of the channel hole 92.

When the elastic member 112 of the tube 55 has a natural length, the outer circumferential surface of the elastic member 112 preferably does not come into contact with any of the first wall surface 102a, the second wall surface 102b and the distal-end face of the retaining plate 98b on the distal-end side of the third wall surface 102c. In addition, the elastic member 112 preferably does not come into any of the first convex portion 84 and the second convex portion 86.

The outer diameter of the pulling member 54 is, for example, about 0.5 mm. The inner diameter of the elastic member 112 is, for example, about 0.8 mm, and the outer diameter of the elastic member 112 is, for example, about 1.3 mm to 1.5 mm. The clearance between the outer circumferential surface of the pulling member 54 and the inner circumferential surface of the elastic member 112 is, for example, about 0.2 mm.

The illumination window 42a of the illumination optical system 42, the observation window 44a of the observation optical system 44, the mouth ring 46c of the distal-end portion of the channel 46, the raising portion 52 of the raising mechanism 48, the pulling member 54, the tube 55, the mouth ring 58a, and the like are properly attached to the distal frame portion 72. In this state, the distal-end cover 14 is attached to the outer circumferences of these components to form the distal-end portion 32.

As shown in FIGS. 7A to 8A, the distal-end cover 14 includes a cover main body 142 attached to the endoscope main body 12 and a wall 144 provided on the cover main body 142.

The cover 14 is formed of a material having electrical insulation properties. The cover 14 is preferably formed of a resin material and/or a rubber material having electrical insulation properties. In the present embodiment, the cover main body 142 of the cover 14 is formed by combining a first structure (main body) 142a made of a resin material and a second structure (retaining ring) 142b made of a rubber material. The first and second structures 142a and 142b are each formed cylindrically.

The first structure 142a is provided outside the distal frame portion 72 to protect the distal frame portion 72, raising portion 52, pulling member (elongated member) 54 and tube 55. The first structure 142a has a blocking portion 152 at its distal end and an annular portion 154, which surrounds the distal frame portion 72, at its proximal end. The blocking portion 152 is formed like a hemispherical surface. The proximal end of the first structure 142a, namely, the proximal end 154a of the annular portion 154 is formed as a proximal-end opening.

Figure 7A:
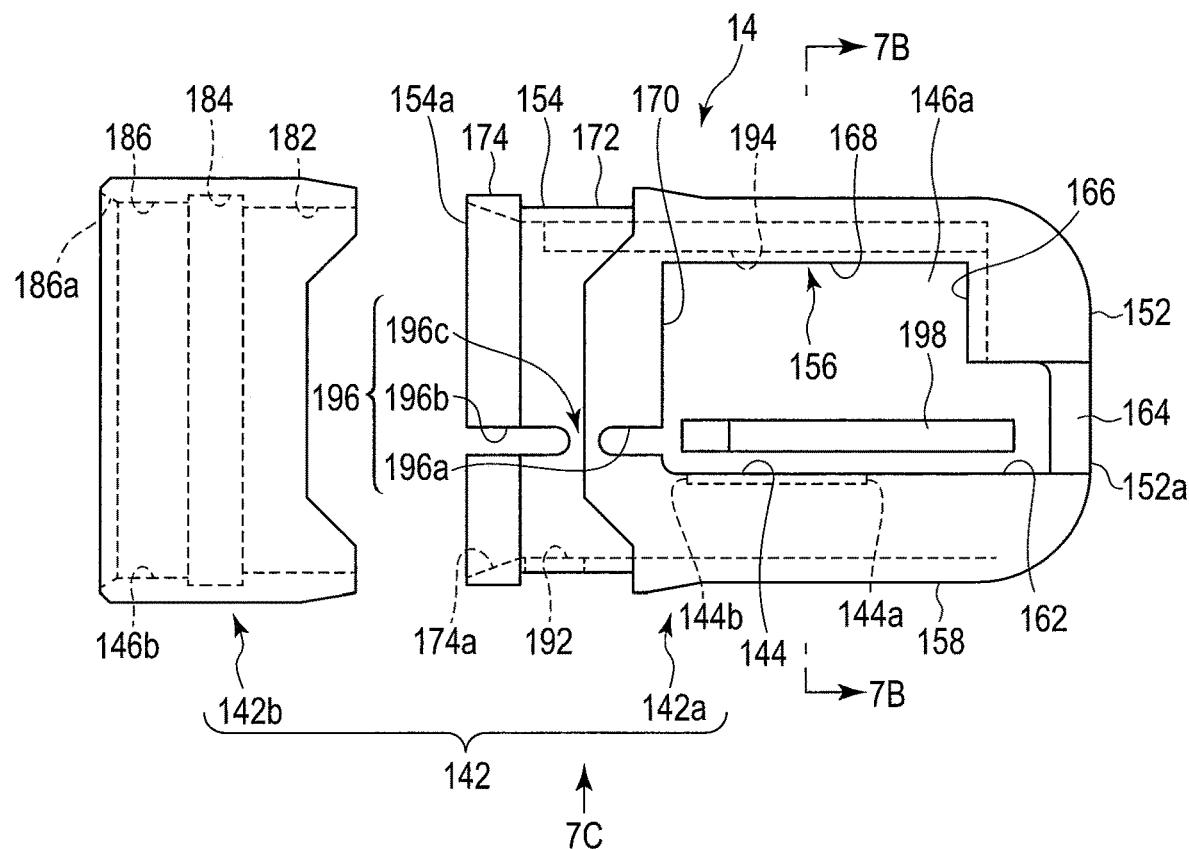
FIG. 7A is a schematic view showing a distal-end cover which is formed by combining two bodies and disposed at the distal-end portion of the insertion portion of the endoscope main body according to the first embodiment.
Figure 7B:
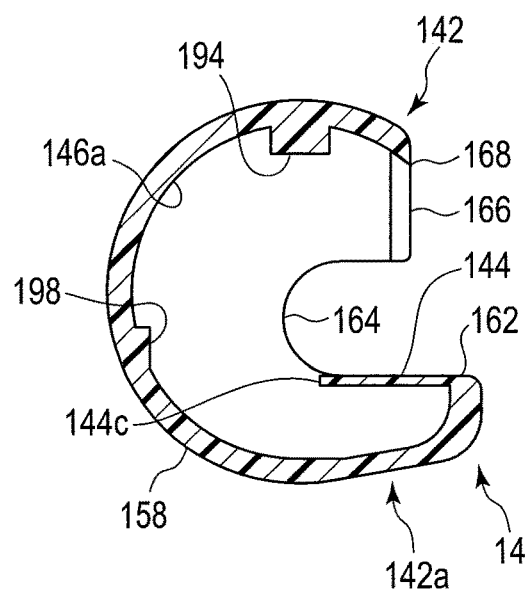
FIG. 7B is a schematic sectional view taken along line 7B-7B in FIG. 7A.

As shown in FIGS. 7A and 7B, the first structure 142a includes an opening edge 156 and a rotating circumferential surface 158 whose cross section is shaped like a letter "C" between the blocking portion 152 and the annular portion 154. The rotating circumferential surface 158 is formed as part of a cylinder. The rotating circumferential surface 158 defines the longitudinal axis (central axis) L of the distal-end portion 32 and the cover 14.

As shown in FIGS. 7A to 8A, the opening edge 156 is opened, for example, in a direction orthogonal to the longitudinal axis L. With the opening edge 156, the illumination window 42a and observation window 44a on the distal-end portion 32, the nozzle 45 and the raising portion 62 are exposed outside the cover 14.

The opening edge 156 includes a right-side edge portion 162 on the right side extending from the proximal-end side to the distal-end side along the longitudinal axis L, a U-shaped concave portion 164 continuous to the right-side edge portion 162, a distal-end side edge portion 166 continuous to the concave portion 164, a left-side edge portion 168 on the left side extending from the proximal side to the distal side along the longitudinal axis L, and a proximal-end side edge portion 170 between the proximal-end portions of the right-side edge portion 162 and left-side edge portion 168. In the opening edge 156, for example, a closed ring is formed by the right-side edge portion 162, concave portion 164, distal-end side edge portion 166, left-side edge portion 168 and proximal-end side edge portion 170. The right-side edge portion 162 and left-side edge portion 168 are preferably parallel or substantially parallel to each other. The distal-end side edge portion 166 and proximal-end side edge portion 170 are preferably parallel or substantially parallel to each other.

The right-side edge portion 162 movably covers the pulling member 54 and tube 55 of the raising mechanism 48 in cooperation with the annular portion 154 and the rotating circumferential surface 158. Similarly, the left-side edge portion 168 covers the left side of the arrangement surface 84a of the first convex portion 84 of the distal frame portion 72 with respect to the illumination window 42a and the observation window 44a in cooperation with the rotating peripheral surface 158. Note that the distal-end side edge portion 166 covers the distal-end side of the arrangement surface 84a of the first convex portion 84 of the distal frame portion 72 with respect to the illumination window 42a in cooperation with the blocking portion 152.

At the distal end of the right-side edge portion 162, the U-shaped concave portion 164 is formed continuously to the right-side edge portion 162. The concave portion 164 is formed toward the distal end 152a of the blocking portion 152. The portion where the concave portion 164 is formed is tapered toward the distal end along the longitudinal axis L.

The annular portion 154 includes, on its outer circumferential surface, a fitting portion 172 into which the second structure 142b is fit. The fitting portion 172 is circumferentially formed at a position apart from the proximal-end side edge portion 170 of the opening edge 156 toward the proximal-end side along the longitudinal axis L. The fitting portion 172 suppresses movement of the second structure 142b along the longitudinal axis L with respect to the first structure 142a and also suppresses movement thereof around the longitudinal axis L. An annular flange portion 174 is formed at the proximal end of the fitting portion 172 of the annular portion 154 so as to project outward in the radial direction of the longitudinal axis L with respect to the fitting portion 172. On the inner periphery of the flange portion 174, a skirt portion 174a is formed to become thinner toward the proximal-end side along the longitudinal axis L. The inner diameter of the skirt portion 174a increases toward the proximal-end side.

A slit 174b is formed in a position including the proximal end 154a of the annular portion 154 of the first structure 142a. Therefore, the inner diameter of the skirt portion 174a can be increased by elastic deformation.

The inner diameter of the inner circumferential surface 146a of the first structure 142a is preferably constant from the vicinity of the distal end of the right-side edge portion 162 of the opening edge 156 and the vicinity of the distal end of the left-side edge portion 168 thereof to the distal end of the skirt portion 174a of the flange portion 174.

Figure 8A:
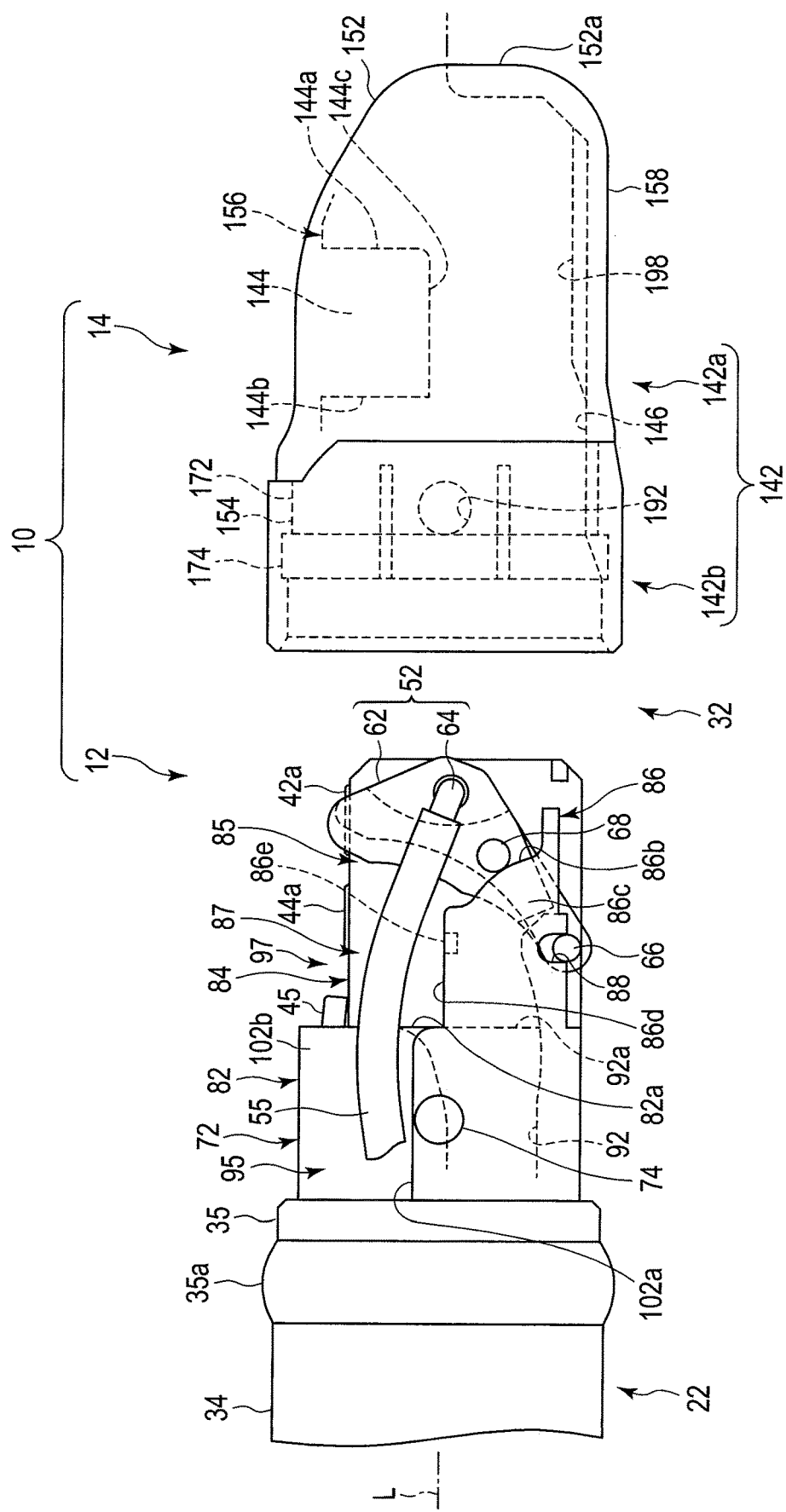
FIG. 8A is a schematic view showing a state in which the distal-end cover according to the first embodiment faces the distal-end portion of the insertion portion of the endoscope main body to use the distal-end cover as an endoscope.

The second structure 142b includes a fitting portion 182 formed on the inner circumferential surface 146b and fit into the fitting portion 172 of the first structure 142a. The second structure 142b retains the outer periphery of the proximal end (proximal-end opening) 154a of the annular portion 154 in a state where the opening edge 156 of the first structure 142a is exposed. The second structure 142b includes an annular fitting concave portion 184 which is formed in the inner circumferential surface 146b and into which the flange portion 174 is fit. Therefore, as shown in FIG. 8A, the second structure 142b is fit into the annular portion 154 of the first structure 142a. Note that the second structure 142b is formed on the inner circumferential surface 146b and includes a fitting portion 186 into which the thread wound portion 35a of the distal-end portion of the bending portion 34 is fit, on the proximal-end side of the fitting concave portion 184. A skirt portion 186a that becomes thinner toward the proximal-end side along the longitudinal axis L is formed on the inner periphery of the proximal end of the fitting portion 186. The inner diameter of the skirt portion 186a increases toward the proximal-end side. The inner diameter of the skirt portion 186a can be increased by elastic deformation.

As shown in FIGS. 7A, 7C and 8A, an engaging concave portion (engaging portion) 192 that can be engaged with the engaging pin 74 is formed on the inner circumferential surface 146a of the annular portion 154 at the proximal end of the first structure 142a. The engaging concave portion 192 engages the first structure 142a with the distal-end portion 32. The engaging concave portion 192 may be formed in a state in which the inner circumferential surface 146a of the first structure 142a and the outer circumferential surface thereof communicate with each other, and may be simply formed concavely with respect to the inner circumferential surface 146a of the first structure 142a. The engaging concave portion 192 is preferably formed in the fitting portion 172.

As shown in FIGS. 7A to 8A, a guide projection portion (second guide) 194 that is movable along the concave portion (guide groove) 84d of the distal frame portion 72, is formed on the inner circumferential surface 146a of the first structure 142a. That is, the guide projection portion 194 project radially inward from the inner circumferential surface 146a of the first structure 142a. In this case, it is preferable that the guide projection portion 194 be formed from the vicinity of the distal end of the inner circumferential surface 146a of the first structure 142a to the vicinity of the proximal end thereof. Though the guide projection 194 can be formed in an appropriate shape, it has substantially a rectangular cross-section. In addition, although not shown, a plurality of guide projection portions 194 may be separated at appropriate intervals.

As shown in FIG. 7A, a fragile portion 196 is formed between the proximal-end side edge portion 170 of the opening edge 156 of the first structure 142a and the proximal end 174a of the flange portion 174 of the annular portion 154. At least part of the fragile portion 196 is provided in the annular portion 154 of the first structure 142a. The fragile portion 196 is so formed that the annular portion 154 is broken by applying stress to the annular portion 154, and its mechanical strength is lower than that of the other part of the annular portion 154. The fragile portion 196 includes slits (grooves) 196a and 196b. The slit 196a is formed continuously with the proximal-end side edge portion 170 of the opening edge 156. The slit 196b is formed continuously with the proximal end 174a of the flange portion 174 of the annular portion 154. The slits 196a and 196b are both formed along the longitudinal axis L. The slits 196a and 196b do not communicate with each other, but a coupling portion 196c is formed between them. Thus, the fitting portion 172 of the annular portion 154 is annular. Note that the engaging concave portion 192 is formed at a position separated from the coupling portion 196c by, e.g. about 90° in the circumferential direction with respect to the longitudinal axis L. The guide projection portion 194 is formed at a position separated from the coupling portion 196c by, e.g. about 90° in the circumferential direction on the side opposite to the engaging concave portion 192 with respect to the longitudinal axis L. The fragile portions 196 are preferably located at a position separated from the guide projection portion 194 and the engaging concave portion 192 by about 90° in the circumferential direction with respect to the central axis C. That is, the guide projection portion 194 differs from the engaging concave portion 192 in the position in the circumferential direction with the longitudinal axis L and is separated therefrom. As will be described later, it is also preferable that the fragile portion 196 is separated from the guide projection portion 194 over 90°, and the distance between the fragile portion 196 and the engaging recess 192 is shorter than the distance between the guide projection portion 194 and the fragile portion 196.

Since the slits 196a and 196b are formed in the fragile portion 196, a thick portion constituting the annular portion 154 is secured only in the portion of the coupling portion 196c. If, therefore, an external stress is applied to the annular portion 154, the stress is concentrated on the coupling portion 196c, and the coupling portion 196c is mechanically broken more easily than the other portion of the annular portion 154. That is, the mechanical strength of the fragile portion 196 is lower than that of the other part of the annular portion 154 as the entire fragile portion including the slits 196a and 196b and the coupling portion 196c.

Instead of the slits (grooves) 196a and 196b, perforations may be formed in the cover main body 142 of the cover 14.

As described above, the fragile portion 196 is formed as a region to be broken when the cover 14 is removed from the distal-end side of the insertion portion 22 of the endoscope main body 12. When the fragile portion 196 is not broken or the fragile portion 196 is not formed, the annular state of the annular portion 154 is maintained without plastic deformation of the cover main body 142 of the cover 14. It is thus difficult to remove the cover 14 from the distal-end side of the insertion portion 22 of the endoscope main body 12.

In the present embodiment, it is preferable that the fragile portion 196 be formed so as to be disposed on the space 95 in which the pulling member 54 moves, not on the arrangement surface 84a of the first convex portion 84 of the distal frame portion 72. The slit 196b on the proximal-end side contributes to elastic deformation of the annular portion 154. That is, when the engaging concave portion 192 is engaged with the engaging pin 74, the flange portion 174 is elastically deformed.

As shown in FIGS. 7A to 8A, a convex portion 198 projecting toward the opening edge 156 is formed at a position opposed to the opening edge 156 on the inner circumferential surface 146 of the cover 14. The convex portion 198 is thicker than the other part of the inner circumferential surface 146 and is formed to have an appropriate length in parallel to the longitudinal axis L. The convex portion 198 can press the pivot shaft 66 of the raising base 62 toward the support portion 88 of the distal frame portion 72. Note that it is preferable that the proximal end of the convex portion 198 have no step or be small and be smoothly continuous with the inner circumferential surface 146a of the cover 14. Therefore, when the cover 14 is to be attached to the distal frame portion 72, the convex portion 198 can be prevented from being hooked on the distal end or the like of the second convex portion 86.

The wall 144 is provided at the opening edge 156, for example. In the present embodiment, the wall 144 is integrated with the right-side edge portion 162 of the first structure 142a of the cover main body 142. The wall 144 extends from the opening edge 156 toward the inner circumferential surface 146a of the first structure 142a opposed to the opening edge 156. The wall 144 is disposed between the raising base 62 and the tube 55. The wall 144 has only to be able to prevent interference between the raising base 62 and the tube 55. Thus, the wall 144 need not be formed from the proximal end to the distal end in the right-side edge portion 162. The wall 144 is preferably disposed in the space 85 and space 87 of the distal frame portion 72.

Note that the shape or material of the wall 144 and tube 55 is suitably selected such that friction between the wall 144 and the tube 55 can be minimized when the tube 55 comes into contact with the wall 144.

The operation of the endoscope 10 according to this embodiment will be described next.

Figure 8B:
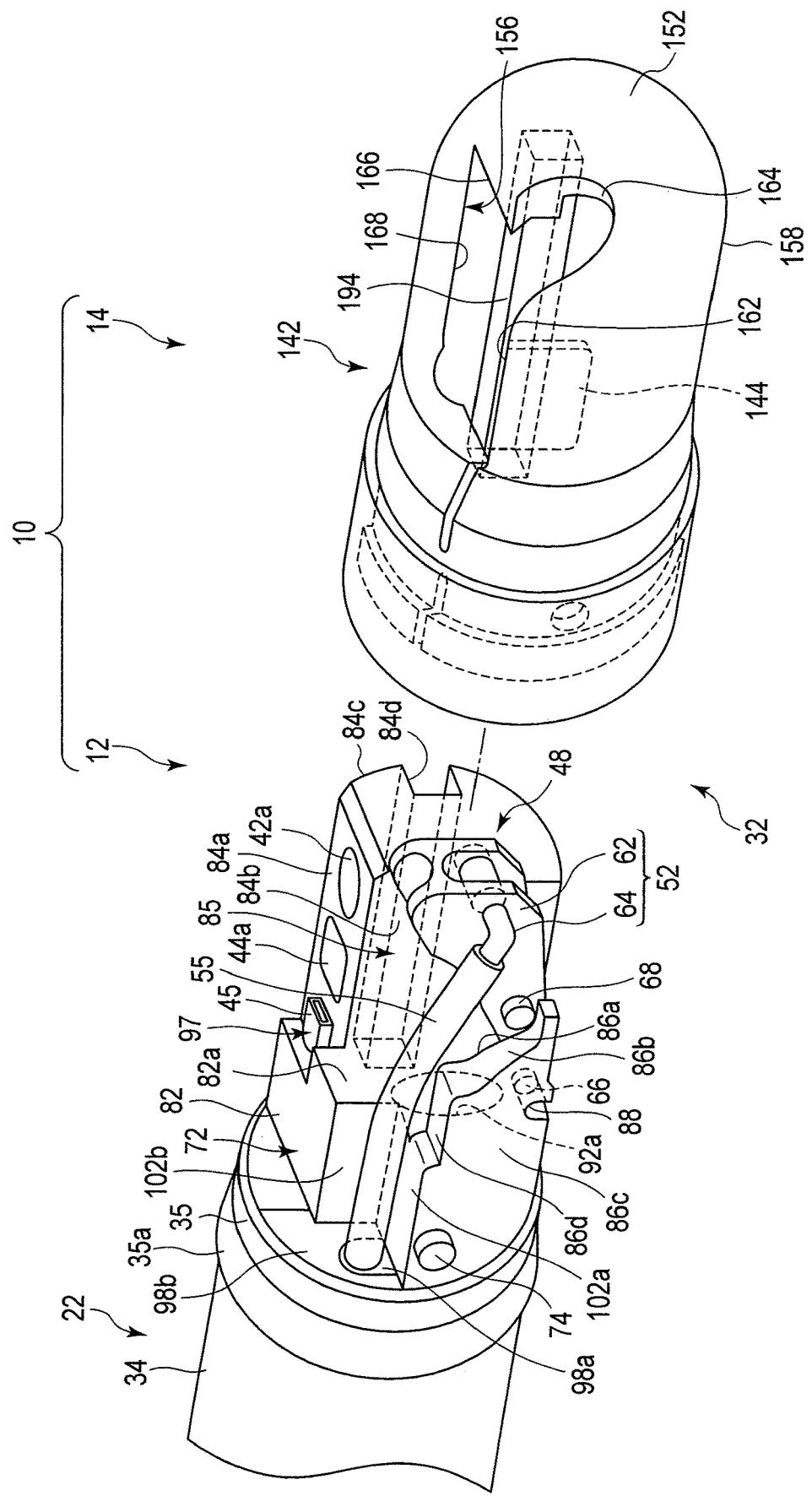
FIG. 8B is a schematic perspective view showing a state in which the distal-end cover shown in FIG. 8A faces the distal-end portion of the insertion portion of the endoscope main body.
Figure 9A:
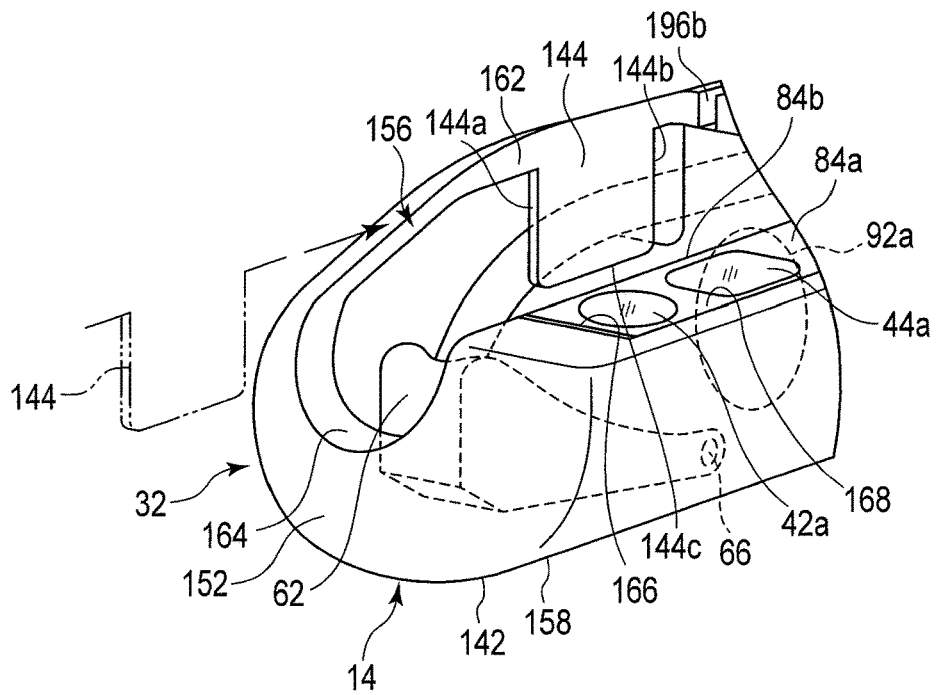
FIG. 9A is a schematic perspective view showing a state in which the distal-end cover shown in FIGS. 8A and 8B is attached to the distal-end portion of the insertion portion of the endoscope main body.
Figure 9B:
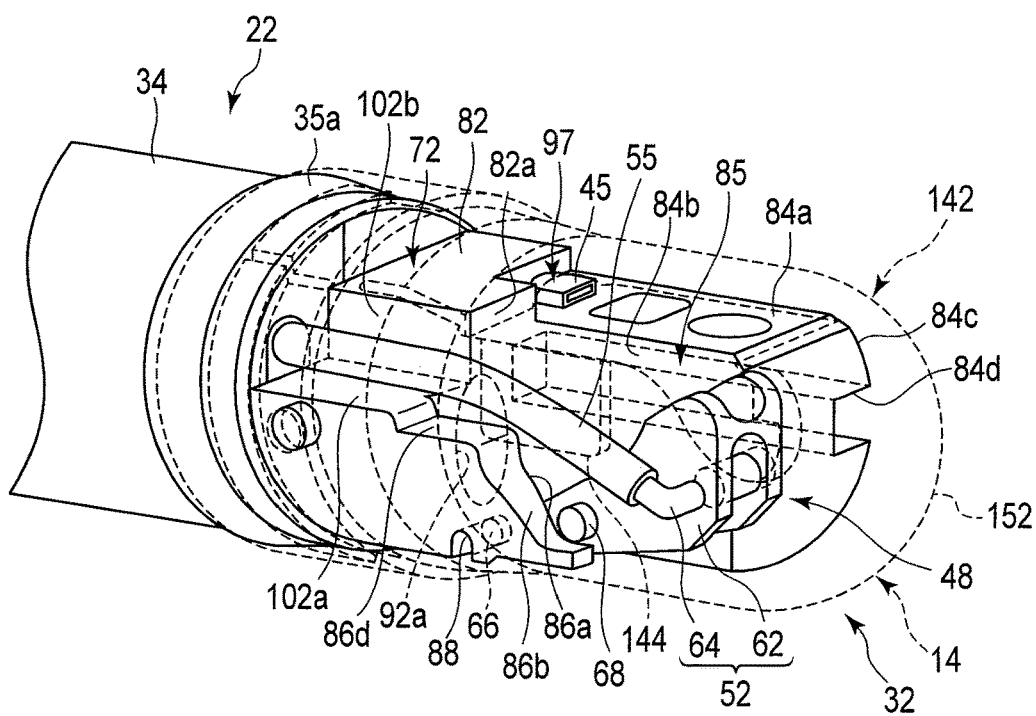
FIG. 9B is a schematic perspective view showing a state in which the distal-end cover shown in FIG. 8B is attached to the distal-end portion of the insertion portion of the endoscope main body.

As shown in FIGS. 8A and 8B, the cover 14 preferably includes a combination of the first and second structures 142a and 142b. Then, the distal-end cover 14 is attached to the distal-end portion 32 of the insertion portion 22 of the endoscope main body 12 by defining the circumferential direction of the longitudinal axis L from the states shown in FIGS. 8A and 8B to the states shown in FIGS. 9A to 9C. At this time, as shown in FIGS. 8B and 9B, the guide projection portion 194 of the cover 14 is fit into the concave portion (guide groove) 84d of the distal frame portion 72 and moved along the longitudinal axis L. The cover 14 is thus prevented from being shifted in position from the distal frame portion 72 in the circumferential direction.

When the cover 14 is attached to the distal-end portion 32, the skirt portion 186a of the fitting portion 186 of the second structure 142b of the cover 14 and the skirt portion 174a of the annular portion 154 of the first structure 142a thereof are sequentially brought into contact with the engaging pin 74 of the distal-end frame portion 72 shown in FIG. 8A. Then, the annular portion 154 is elastically deformed by the slit 196b. The engaging concave portion 192 is thus engaged with the engaging pin 74. Then, the cover 14 is prevented from being shifted in position from the distal-end portion 32 in the axial and circumferential directions.

Note that the proximal-end side edge portion 144b of the wall 144 can be brought into contact with the distal end 82a of the base portion 82 of the distal frame portion 72 when the distal-end cover 14 is attached to the distal-end portion 32 of the endoscope main body 12. The proximal-end side edge portion 144b of the wall 144 can thus be used for axial positioning of the distal-end cover 14 with respect to the distal frame portion 72.

Figure 10A:
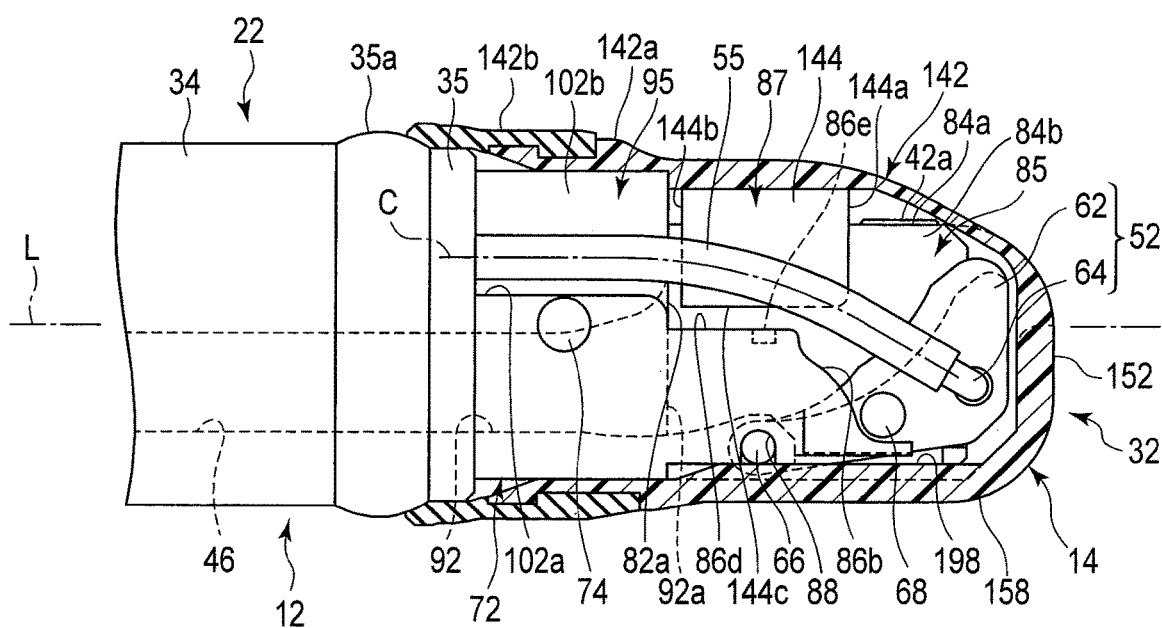
FIG. 10A is a schematic partial sectional view showing a state of the tube inside which a raising portion and a pulling member for operating the raising portion are disposed with respect to the wall of the distal-end cover when the distal-end cover is attached to a distal-end portion of the insertion portion of the endoscope main body and the raising portion is disposed in the lowered position.
Figure 10B:
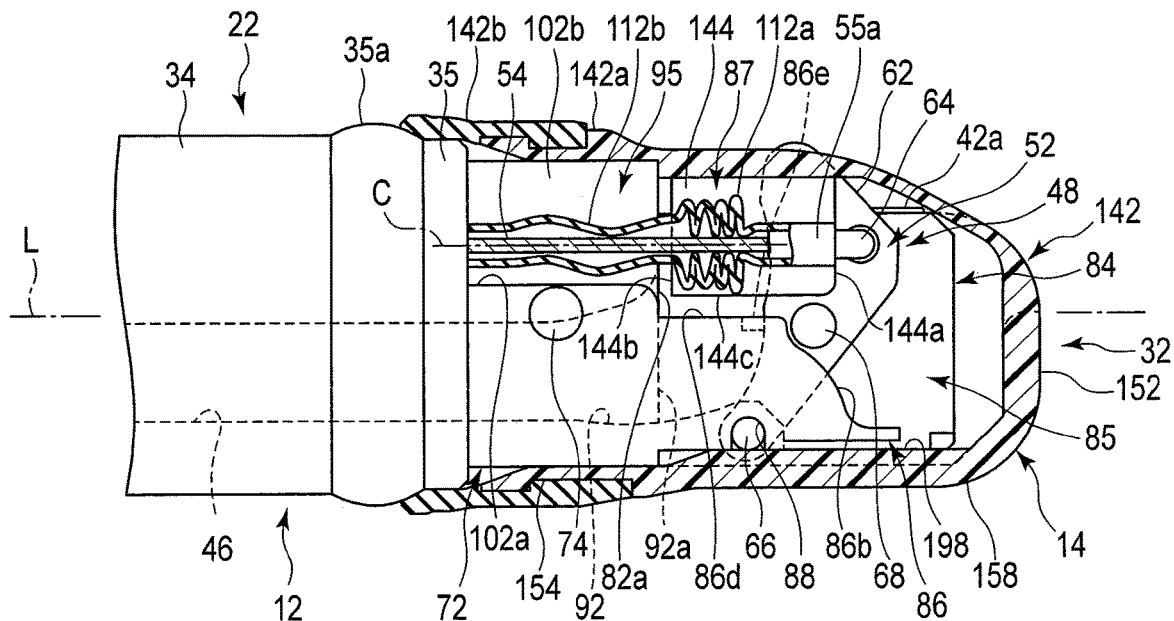
FIG. 10B is a schematic partial sectional view showing a state of the tube inside which the raising portion and the pulling member for operating the raising portion are disposed with respect to the wall of the distal-end cover when the distal-end cover is attached to the distal-end portion of the insertion portion of the endoscope main body and the raising portion is disposed in the raised position.
Figure 10C:
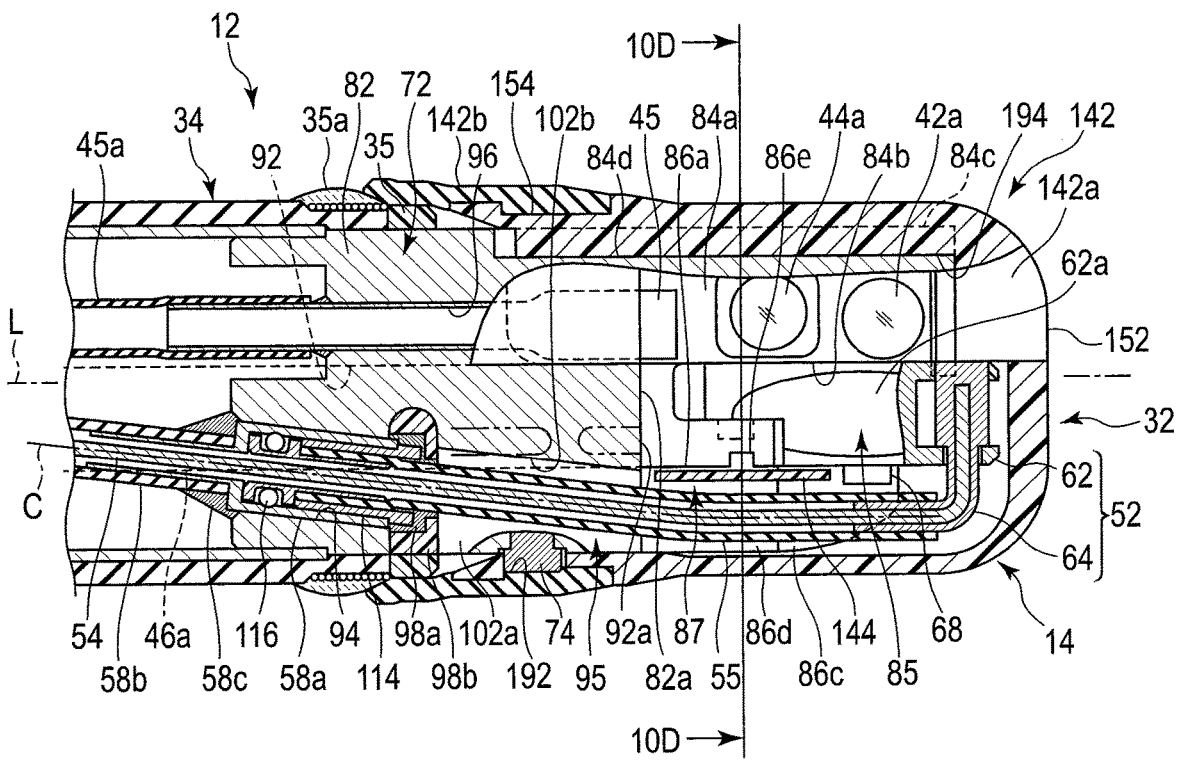
FIG. 10C is a schematic partial sectional view different from that of FIG. 10A, showing a state in which the raising base of the distal-end portion of the insertion portion of the endoscope according to the first embodiment is disposed in a lowered position.

As the cover 14 is attached to the distal-end portion 32 while it is prevented from being shifted in position, the convex portion 198 of the inner circumferential surface 146a of the cover 14 shown in FIG. 8A presses the pivot shaft 66 of the raising portion 52 toward the support portion 88 of the distal frame portion 72. The convex portion 198 protrudes from the inner circumferential surface 146a toward the opening edge 156. The convex portion 198 is thicker than, for example, other portions adjacent to the convex portion 198. Even though the other portions adjacent to the convex portion 198 are thus thinner as shown in FIGS. 10A to 10C, the first structure 142a of the cover 14 prevents the pivot shaft 66 of the raising portion 52 from coming off from the support portion 88 of the distal frame portion 72 against an external force including the gravity of the raising portion 52. Thus, the pivot shaft 66 of the raising portion 52 is rotatably supported by the support portion 88 of the distal frame portion 72, and this support state is maintained. That is, when the cover 14 is attached to the outside of the distal frame portion 72 of the distal-end portion 32, the pivot shaft 66 of the raising portion 52 is positioned on the inner circumferential surface of the distal-end cover 14 relative to the distal frame portion 72 as the wall 144 is provided between the tube 55 and the raising base 62.

The convex portion 198 is formed to have an appropriate length along the longitudinal axis L. The support portion 88 is brought into contact with the convex portion 198. Thus, contaminants and the like are prevented as much as possible from entering between the convex portion 198 of the cover 14, the pivot shaft 66 of the raising portion 52 and the support portion 88 of the distal frame portion 72.

When the cover 14 is attached to the distal-end portion 32 of the endoscope main body 12 while it is prevented from being shifted in position as shown in FIGS. 9A to 10D, the wall 144 is inserted in the space 85 and the space 72 in sequence from the distal-end side of the distal frame portion 72. The raising base 62 is located in a lowered position, and the cover 14 is prevented from being shifted in position in the circumferential direction. The wall 144 is thus prevented from coming into contact with the raising base 62 and the tube 55. That is, the wall 144 is prevented from interfering with the raising base 62 and the tube 55. The wall 144 is disposed between the raising base 62 and the tube 55.

The cover 14 covers the outer circumferential surface of the base portion 82 of the distal frame portion 72 and also covers the outer circumferential surface 84c of the first convex portion 84 and the outer circumferential surface 86c of the second convex portion 86. The opening edge 156 of the cover 14 exposes the illumination window 42a of the illumination optical system 42 and the observation window 44a of the observation optical system 44 toward the outside of the endoscope 10. The opening edge 156 of the cover 14 also exposes the space 85 in which the raising base 62 is disposed, toward the outside of the endoscope 10. The inner circumferential surface 146a and the distal frame portion 72 of the cover 14 define the space 85, space 87 and space 95, and cooperate with the inner circumferential surface 146 of the cover 14 to define a movable region of the pulling member 54 and the elastic member 112.

Figure 9C:
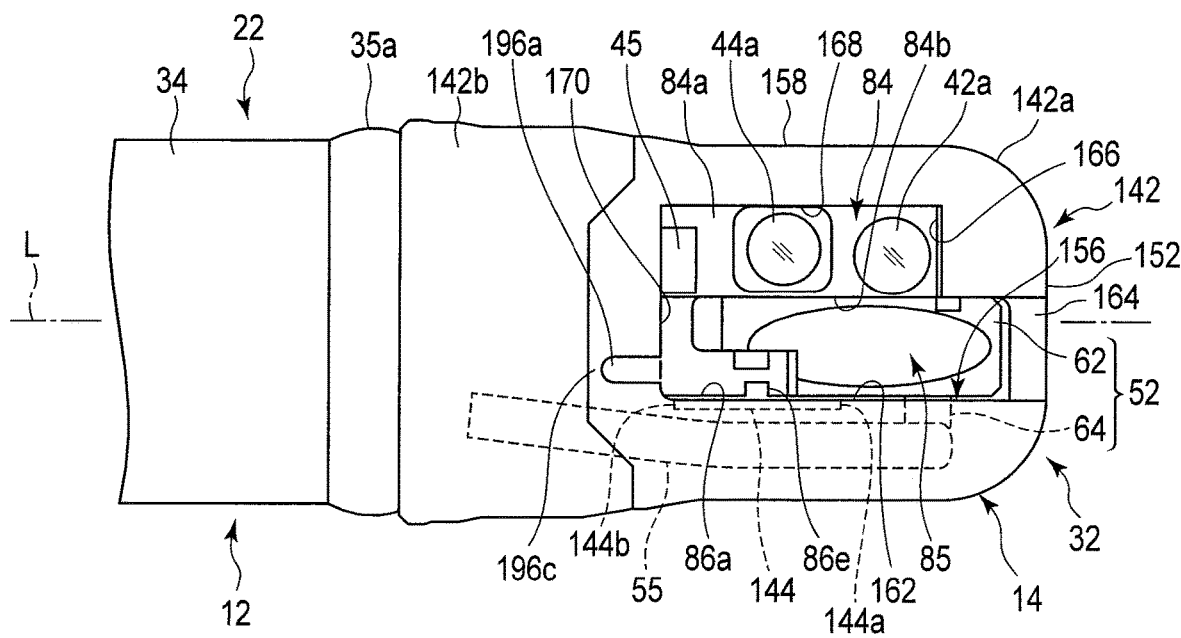
FIG. 9C is a schematic view showing a state in which the distal-end cover according to the first embodiment is attached to the distal-end portion of the insertion portion of the endoscope main body.
Figure 10D:
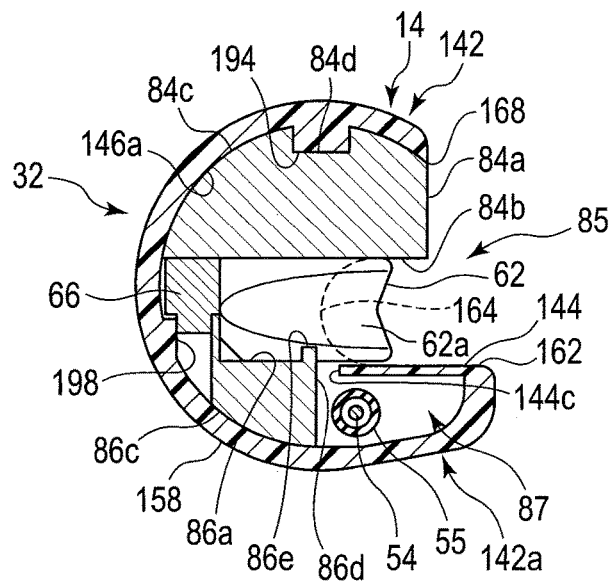
FIG. 10D is a schematic sectional view taken along line 10D-10D in FIG. 10C.

At this time, as shown in FIGS. 9C and 10D, the illumination window 42a, observation window 44a and nozzle 45 are exposed to the opening edge 156 of the cover 14, and the raising base 62 is exposed such that it can be swung in an appropriate range. When a treatment instrument (not shown) is guided by the raising base 62 and protrudes from the distal end of the raising base 62, it can be prevented from interfering with the cover 14 by the concave portion 164 of the opening edge 156. Note that a gap is formed between the raising base 62 and the cover 14. Even though the raising base 62 is swung, the amount of gap between the raising base 62 and the cover 14 varies, but the gap is maintained. Thus, a hinderance of the cover 14 to the movement of the raising base 62 is prevented.

When the lever 56 supported by the operation portion 24 shown in FIG. 1 is operated, the raising portion 52 supported by the distal frame portion 72 is moved in conjunction with the pulling member 54. When the lever 56 is pushed up the most (first position), the raising portion 52 is disposed at the lowered position shown in FIG. 10A. Then, the pulling force on the pulling member 54 is released, and the pulling member 54 is moved to the most distal-end side. As the lever 56 is pushed down, the pulling member 54 is pulled toward the proximal-end side, and the raising portion 52 is rotated about the pivot shaft 66 supported by the support portion 88 of the distal frame portion 72. The raising portion 52 is thus placed at the raised position shown in FIG. 10B while the lever 56 is pushed down the most (second position).

Incidentally, when the lever 46 is in the first position, it is prevented from moving unintentionally from the first position to the second position by the elastic force of the pulling member 44, the tube 45 and the like, with the result that the operation portion 42 is prevented from swinging unintentionally.

The lever 56 shown in FIG. 1 is placed in the first position, and the raising portion 52 is placed in the lowered position shown in FIG. 10A. The elastic member 112 of the tube 55 outside the pulling member 54 has a natural length. No creases are caused in the elastic member 112 of the tube 55. Alternatively, the creases in the elastic member 112 of the tube 55 are lengthened the most.

The lever 56 shown in FIG. 1 is disposed in the second position, and the raising portion 52 is disposed in the raised position shown in FIG. 10B. Though one end 55a of the tube 55 is movable relative to the distal frame portion 72, the other end 55b is fit to the distal frame portion 72 and thus it cannot be moved. For this reason, when the pulling member 54 is pulled by the operation of the lever 56 to move the raising portion 52 from the lowered position to the raised position, the one end 55a of the tube 55 moves toward the other end 55b. A compressive force is then applied to the elastic member 112 of the tube 55 to shrink from its natural length along the central axis C of the elastic member 112. Thus, when the raising portion 52 is in the raised position, creases are formed in the elastic member 112 of the tube 55.

The elastic member 112 is formed such that the distal-end portion 112a is more easily deformed to be compressed in a direction along the central axis C of the elastic member 112 (length direction) than the proximal-end side portion 112b. Thus, the distal-end side portion 112a of the elastic member 112 is greatly deformed, and the proximal-end side portion 112b thereof is deformed less than the distal-end side portion 112a. When a compressive force by which the elastic member 112 is shrunk from the natural length is applied to the elastic member 112, the proximal-end side portion 112b is deformed into, e.g. a wave shape from the straight state shown in FIG. 10A to a state in which the inner and outer diameters of the elastic member 112 are substantially maintained as shown in FIG. 10B. The proximal-end side portion 112b is deformed into a wave shape and is not deformed to cause creases. A plurality of creases are formed in the distal-end side portion 112a from the state shown in FIG. 10A without maintaining the inner and outer diameters of the elastic member 112 as shown in FIG. 10B. In the elastic member 112 of the tube 55, therefore, the distal-end side portion 112a is more easily deformed to cause continuous compressed creases along the central axis C of the pulling member 54 and the elastic member 112 of the tube 55 than the proximal-end side portion 112b. That is, in the elastic member 112 of the tube 55, the distal-end side portion 112s, which is a portion disposed between the distal-end opening 92a of the first cylindrical surface 92 and the raising portion 52, is more easily deformed to cause continuous compressed creases along the central axis C of the tube 94 than the proximal-end side portion 112b that is a portion disposed between the distal end 94a of the passage 94 and the distal-end opening 92a of the channel hole 92. Therefore, the creases caused in the elastic member 112 are formed chiefly in the distal-end side portion 112a and are prevented from being formed in the proximal-end side portion 112b.

As shown in FIG. 10B, the creases are formed chiefly in the space 87 (see FIG. 4B). The wall 144 is disposed between the raising base 62 and the tube 55 at a position including the space 87. The wall 144 may be in contact with the distal-end side portion 112a of the elastic member 112 of the creased tube 55 on the opposite surface of the side facing the raising base 62. Even in this case, the wall 144 prevents the distal-end side portion 112a of the creased tube 55 from coming into contact with the raising base 62. Therefore, the wall 144 prevents the tube 55 from interfering with the raising base 62.

When the endoscope 10 is in use, the guide path 62a of the raising base 62 guides the treatment instrument by operation between the lowered position (see FIGS. 10A, 3A and 3B) and the raised position (see FIGS. 10B, 4A and 4B), and changes the direction of the distal end of the treatment instrument to a direction away from the direction along the longitudinal axis L of the insertion portion 22. At this time, the treatment instrument receives not only a reaction force from the guide path 62a but also an external force such as gravity. For this reason, the treatment instrument is likely to come off from the guide path 62a of the raising base 62. Even in this case, the wall 144 prevents the treatment instrument from coming into contact with the tube 55. Therefore, the life of the tube 55 can be made longer than when the tube 55 is in contact with the raising base 62 and/or the treatment instrument.

When the tube 55 is moved with the outer circumferential surface of the elastic member 112 of the tube 55 in contact with the wall 144 of the cover 14, friction occurs between the outer circumferential surface of the elastic member 112 of the tube 55 and the wall 144 of the cover 14. A space between the outer circumferential surface of the elastic member 112 of the tube 55 and the wall 144 of the cover 14 is formed in a shape that minimizes the friction, and a material is selected. Thus, friction generated between the outer circumferential surface of the elastic member 112 of the tube 55 and the wall 144 of the cover 14 is minimized.

When a plurality of creases are formed in the distal-end side portion 112a of the elastic member 112 of the tube 55, the outer circumferential surface of the pulling member 54 easily comes into contact with the inner circumferential surface of the distal-end side portion 112a of the elastic member 112. However, the moving amount of the pulling member 54 relative to the elastic member 112 of the tube 55 is smaller toward the distal end (one end 55a of the tube 55) of the elastic member 112. Therefore, friction generated between the outer circumferential surface of the pulling member 54 and the inner circumferential surface of the distal-end side portion 112a of the elastic member 112 is minimized.

As described above, the proximal-end side portion 112b of the elastic member 112 of the tube 55 is disposed along the longitudinal axis L between the distal end 94a of the passage 94 and the distal-end opening 92a of the first cylindrical surface (channel hole) 92. That is, the proximal-end side portion 112b of the elastic member 112 of the tube 55 allows the proximal-end side portion 112b to be deformed and is disposed in an appropriate space 95 formed between the proximal-end side portion 112b and the inner circumferential surface 146 of the distal-end cover 14. The proximal-end side portion 112b of the elastic member 112 of the tube 55 is prevented from being deformed so as to be compressed in its length direction. Thus, the proximal-end side portion 112b of the elastic member 112 of the tube 55 is deformed into, e.g. a wave shape. The proximal-end side portion 112b is prevented from coming into contact with the first wall surface 102a, second wall surface 102b and inner circumferential surface 146 of the distal-end cover 14. Therefore, the deformation of the proximal-end side portion 112b of the elastic member 112 is suppressed within the range of the space 95. Since the deformation of the proximal-end side portion 112b of the elastic member 112 of the tube 55 is suppressed, the proximal-end side portion 112b is prevented from coming into contact with the inner circumferential surface 146 of the distal-end cover 14 even though it is deformed.

Furthermore, the amount of movement of the pulling member 54 to the raising portion 52 increases from the one end 55a toward the other end 55b, and a clearance between the inner circumferential surface of the proximal-end side portion 112b and the pulling member 54 is maintained as appropriate. Therefore, friction generated between the outer circumferential surface of the pulling member 54 and the inner circumferential surface of the proximal-end side portion 112b of the elastic member 112 is minimized.

In the sheet of FIG. 10B, the extension surface 86d of the second convex portion 86 that forms the space 87 is located lower than the position of the first wall surface 102a on the distal-end side of the second cylindrical surface 94 that forms the space 95. In the sheet of FIG. 4B, the defining surface 84b of the first convex portion 84 that forms the space 87 is located on the right side more than the position of the second wall surface 102b on the distal-end side of the second cylindrical surface 94 that forms the space 95. The space 87 is formed larger in the vertical and width directions than the space 95. As shown in FIG. 10 (FIG. 4B), the length La of the part of the distal-end side portion 112a of the elastic member 112 of the tube 55 where creases are formed, in the direction along the central axis (longitudinal axis) C of the elastic member 112, is shorter than the length Lb of the part where the proximal-end side portion 112b is deformed in the direction along the central axis (longitudinal axis) C of the elastic member 112. The elastic member 112 of the tube 55 is thus kept in the range of the space 86 even though the distal-end side portion 112a expands in the vertical and width directions when creases are formed. Even though the distal-end side portion 112a of the elastic member 112 of the tube 55 is deformed to form a plurality of creases, the deformed distal-end side portion 112a is prevented from coming into contact with the first convex portion 84 and second convex portion 86 of the distal frame portion 72 and the inner circumferential surface 146 of the distal-end cover 14.

Figure 11:
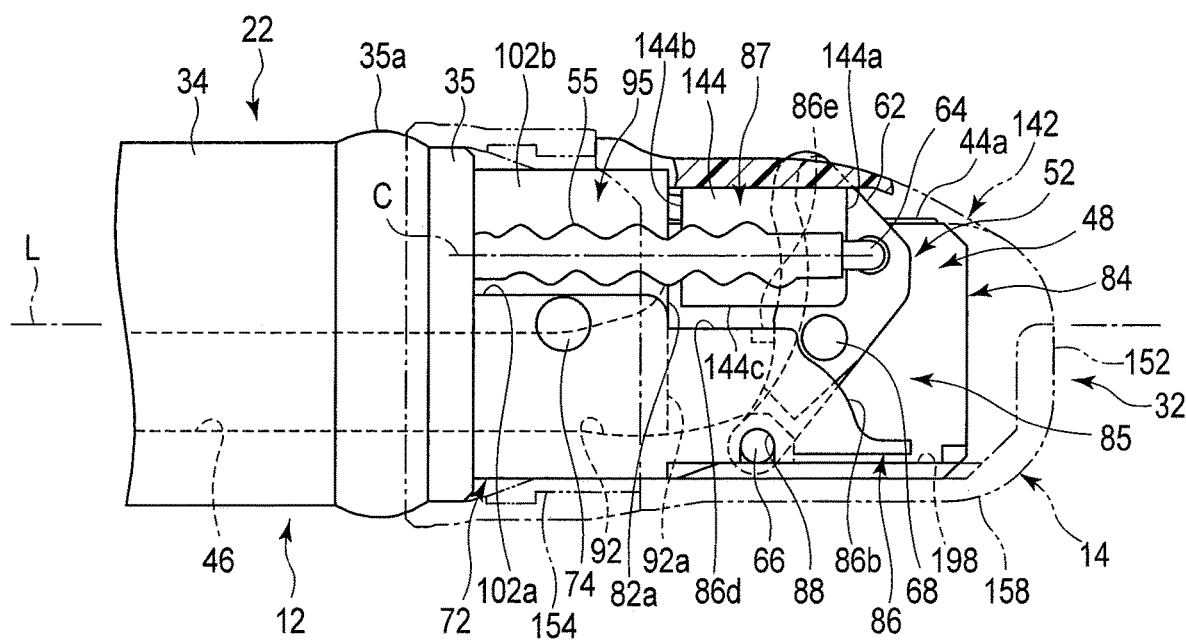
FIG. 11 is a schematic partial sectional view showing a state of a tube inside which the raising portion and the pulling member for operating the raising portion are disposed with respect to the wall of the distal-end cover when the distal-end cover is attached to the distal-end portion of the insertion portion of the endoscope main body and the raising portion is disposed in the raised position, when the tube differs in property from the tube shown in FIG. 10B.

Unlike in the example shown in FIG. 10B, as shown in FIG. 11, the tube 55 can be formed such that the space between the distal-end side portion 112a and the proximal-end side portion 112b is deformed into substantially a uniform wave shape when a compressive force is applied along the central axis C by material adjustment and the like. In this case, the maximum outer diameter of the tube 55 when it is deformed can be made smaller than that when creases are formed in the distal-end side portion 112a of the tube 55. Thus, even though the tube 55 is entirely deformed into a wave shape when the raising portion 52 is disposed in the raised position, the wall 144 prevents the tube 55 from interfering with the raising base 62.

When the pulling of the pulling member 54 is released by the lever 56 to move the raising portion 52 from the raised position to the lowered position, the one end 55a of the tube 55 moves in a direction away from the other end 55b along the central axis C of the elastic member 112. Then, the compressive force (shrinkage) of the tube 55 with respect to the elastic member 112 is gradually released and returned to the natural length.

After the endoscope 10 is used, the distal-end cover 14 is removed from the distal-end portion 32 of the endoscope main body 12. In this case, the right-side edge portion 162 of the opening edge 156 of the distal-end cover 14 is pressed against the distal-end portion 32 of the endoscope main body 12 so as to increase the distance from the left-side edge portion 168 to the longitudinal axis L and the central axis C. Since the projection portion 194 of the cover 14 is fit into the concave portion (guide groove) 84d of the distal frame portion 72, the cover 14 is prevented from moving about the longitudinal axis L with respect to the distal-end portion 32. Therefore, when a load is applied to the cover 14, the coupling portion 196c of the fragile portion 196 separated from the projection portion 194 is broken. In addition, as the coupling portion 196c is broken, the engagement between the engaging concave portion 192 of the cover 14 and the engaging pin 74 of the distal-end portion 32 is disengaged.

As the coupling portion 196c is broken, the wall 144 is likely to apply a load to separate the tube 55 and the pulling member 54 from the defining surface (plane) 84b of the first convex portion 84 of the distal frame portion 72. The wall 144 is formed of a thin resin material that is integrated with the first structure 142a as one component. The wall 144 is thus prevented from applying a load to damage the tube 55 and/or the pulling member 54.

Then, the distal-end cover 14 is moved toward the distal end along the longitudinal axis L with respect to the distal-end portion 32 to release the fitting of the projection portion 194 of the cover 14 into the concave portion (guide groove) 84d of the distal frame portion 72 and remove the cover 14 from the distal-end portion 32.

Incidentally, as the cover 14 is removed from outside the distal frame portion 72 of the distal-end portion 32 and the wall 144 is moved out from between the tube 55 and the raising portion 52, the support of the pivot shaft 66 of the raising portion 52 on the convex portion 198 of the inner circumferential surface 146 of the cover 14 is released. Thus, the positioning of the pivot shaft 66 of the raising portion 52 with respect to the distal frame portion 72 is released.

The removed cover 14 is discarded. The endoscope main body 12 is cleaned. The distal-end portion 32 of the endoscope main body 12 is cleaned as appropriate using a brush or the like. At this time, the fitting of the pivot shaft 66 of the raising portion 52 into the support portion 88 of the distal frame portion 72 can be released. Thus, the support portion 88 on which the raising portion 52 is supported is also easily cleaned. Then, the endoscope main body 12 is disinfected and sterilized for reuse.

As described above, the following can be said about the endoscope 10 according to the present embodiment.

The wall 144 is provided between the tube 55 inside which the pulling member 54 is disposed and the raising portion 52. The wall 144 is formed in the distal-end cover 14 of the endoscope 10. According to the present embodiment, therefore, there can be provided the distal-end cover 14 for the endoscope 10, which can prevent the tube 55 outside the pulling member 54 from coming into contact with the raising portion 52, and the endoscope 10, even though the raising portion 52 is operated in accordance with the movement of the pulling member 54. According to the present embodiment, there can also be provided the distal-end cover 14 for the endoscope 10, which can prevent the tube 55 outside the pulling member 54 from coming into contact with the raising portion 52 and the treatment instrument, and the endoscope 10, even though the treatment instrument is moved in accordance with the operation of the raising portion 52.

When the endoscope 10 is used, the wall 144 is provided between the raising base 62 and the tube 55. The wall 144 can thus prevent contaminants and the like from entering the tube 55 from the raising base 62 through the opening edge 156 of the cover 14. On the other hand, when the cover 14 is removed from the distal-end portion 32, the wall 144 is removed from the distal-end portion 32. Thus, the raising portion 52 of the raising mechanism 48 of the distal-end portion 32 and its vicinity can easily be cleaned. Therefore, the wall 144 provided in the main body 142 of the cover 14 can be prevented from affecting the cleanability of the distal-end portion 32 of the endoscope main body 12 using a brush or the like.

It is preferable that the distal-end side portion 112a of the tube 55 be more easily deformed than the proximal-end side portion 112b thereof. Since the wall 144 is disposed between the distal-end side portion 112a of the tube 55 and the raising base 62 when the raising portion 52 is raised, it can prevent the deformed distal-end side portion 55a of the tube 55 from coming into contact with the raising base 62.

When the raising base 62 is moved to the raised position and brought into contact with the projection 86e formed on the defining surface 86a of the second convex portion 86, a distal-end side edge portion 144a of the wall 144 according to the present embodiment may be brought close to or brought into contact with the raising base 62. At this time, distal-end side edge portion 144a of the wall 144 can define the maximum position at which the raising base 62 is raised.

First Modification

A first modification to the distal-end cover 14 will be described below with reference to FIG. 12.

Figure 12:
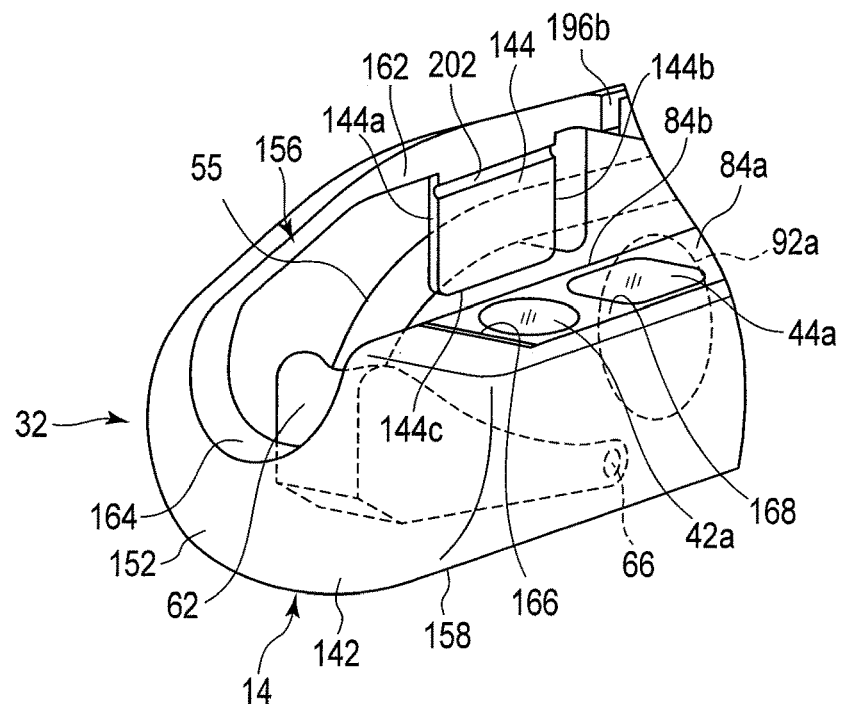
FIG. 12 is a schematic perspective view showing a state in which a distal-end cover according to a first modification to the first embodiment is attached to the distal-end portion of the insertion portion of the endoscope main body shown in FIGS. 8A and 8B.

As shown in FIG. 12, a fragile portion 202 is formed between the right-side edge portion 162 and the wall 144. As described above, when the cover 14 is removed from the distal-end portion 32 of the insertion portion 22 of the endoscope main body 12, the wall 144 presses the tube 55 and the pulling member 54 in a direction away from the raising base 62. In this case, a load is likely to be applied to the tube 55 and the pulling member 54. When the first structure 142a of the distal-end cover 14 is removed from the endoscope main body 12 by the fragile portion 202, the wall 144 is bent by the pressure from the tube 55 (and the pulling member (elongated member) 54 disposed inside the tube 55). Thus, when the wall 144 receives reaction force from the tube 55 (and the pulling member 54), it is deformed or broken such that the fragile portion 202 suppresses the load applied by the wall 144. Therefore, when the cover 14 is removed from the distal-end portion 32 of the insertion portion 22 of the endoscope main body 12, the wall 144 can be prevented as much as possible from applying a load to the tube 55 and the pulling member 54.

Second Modification

A second modification to the distal-end cover 14 will be described below with reference to FIG. 13.

Figure 13:
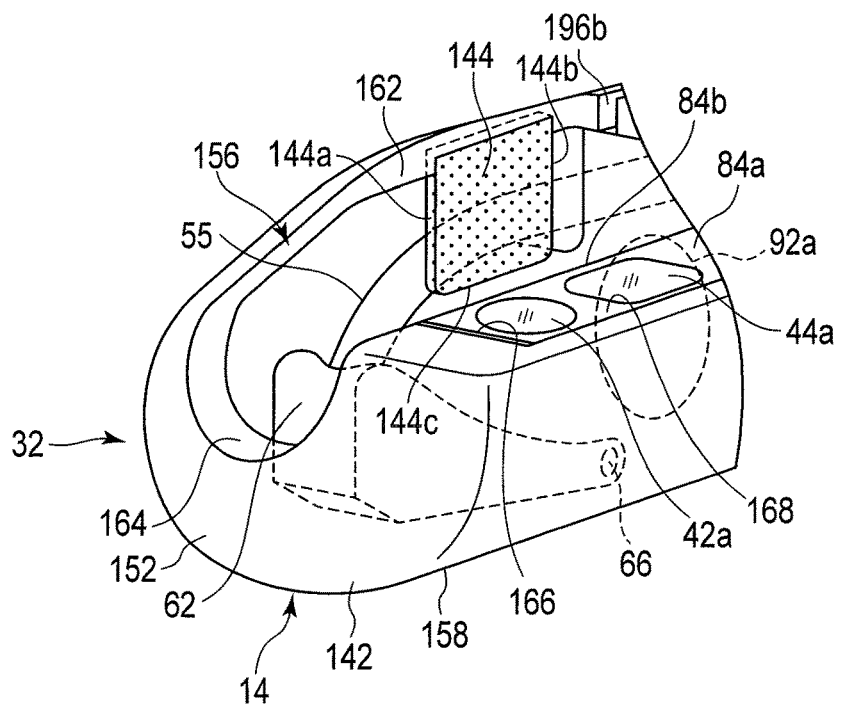
FIG. 13 is a schematic perspective view showing a state in which a distal-end cover according to a second modification to the first embodiment is attached to the distal-end portion of the insertion portion of the endoscope main body shown in FIGS. 8A and 8B.

As shown in FIG. 13, the wall 144 is fixed to the right-side edge portion 162 of the opening edge 156 with a rubber material that is separate from the first structure 142a. As described above, when the cover 14 is removed from the distal-end portion 32 of the insertion portion 22 of the endoscope main body 12, the wall 144 presses the tube 55 and the pulling member 54 in a direction away from the raising base 62. In this case, a load is likely to be applied to the tube 55 and the pulling member 54. If, however, the wall 144 receives reaction force from the tube 55 and the pulling member 54, the wall 144, which is made of a rubber material, is deformed to suppress the load applied by the wall 144. Therefore, when the cover 14 is removed from the distal-end portion 32 of the insertion portion 22 of the endoscope main body 12, the wall 144 can prevent a load from being applied to the tube 55 and the pulling member 54 as much as possible. That is, the wall 144 made of a rubber material according to the present modification is used as a portion to be deformed by the tube 55 and the pulling member 54 when the first structure (cover main body) 142a is removed from outside the distal frame portion 72.

Third Modification

A third modification to the distal-end cover 14 will be described below with reference to FIG. 14.

Figure 14:
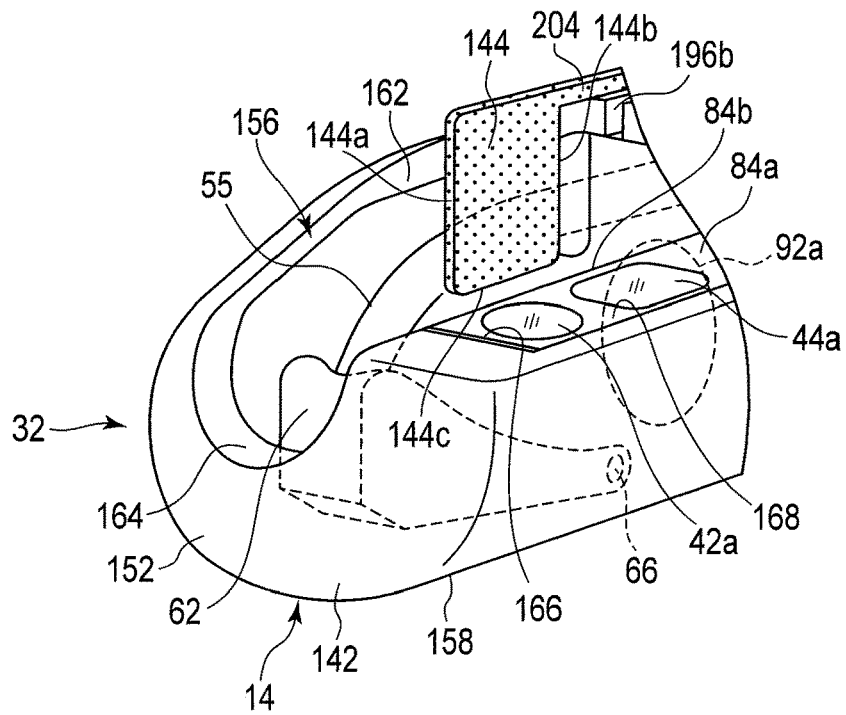
FIG. 14 is a schematic perspective view showing a state in which a distal-end cover according to a third modification to the first embodiment is attached to the distal-end portion of the insertion portion of the endoscope main body shown in FIGS. 8A and 8B.

As shown in FIG. 14, the wall 144 is integrated with the second structure 142b as one component by means of an arm 204. That is, the wall 144 is formed at the distal end of the second structure 142b. It is preferable that the wall 144 be in contact with the right-side edge portion 162 of the opening edge 156 of the first structure 142a. As described above, when the cover 14 is removed from the distal-end portion 32 of the insertion portion 22 of the endoscope main body 12, the wall 144 presses the tube 55 and the pulling member 54 in a direction away from the raising base 62. In this case, a load is likely to be applied to the tube 55 and the pulling member 54. If, however, the wall 144 receives reaction force from the tube 55 and the pulling member 54, the wall 144, which is made of a rubber material, is deformed to suppress the load applied by the wall 144. Therefore, when the cover 14 is removed from the distal-end portion 32 of the insertion portion 22 of the endoscope main body 12, the wall 144 can prevent a load from being applied to the tube 55 and the pulling member 54 as much as possible. That is, the wall 144 made of a rubber material according to the present modification is used as a portion to be deformed by the tube 55 and the pulling member 54 when the first structure (cover main body) 142a is removed from outside the distal frame portion 72.

Fourth Modification

A fourth modification to the distal-end cover 14 will be described below with reference to FIG. 15.

Figure 15:
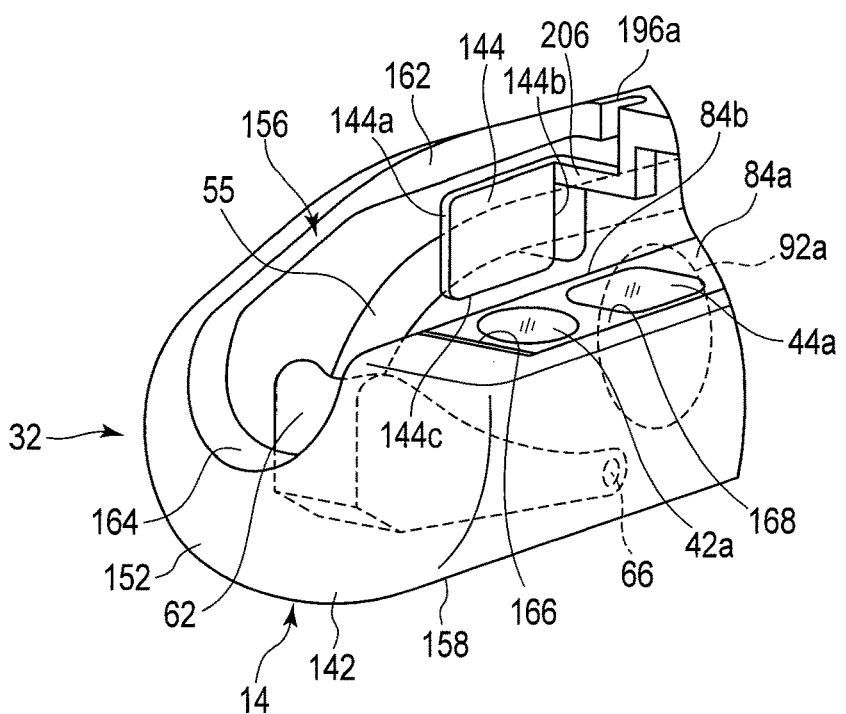
FIG. 15 is a schematic perspective view showing a state in which a distal-end cover according to a fourth modification to the first embodiment is attached to the distal-end portion of the insertion portion of the endoscope main body shown in FIGS. 8A and 8B.

In the distal-end cover 14 shown in FIG. 15, the wall 144 is integrated with not the right-side edge portion 162 but the proximal-end side edge portion 170 of the opening edge 156 of the first structure 142a. The wall 144 extends from a position closer to the left-side edge portion 168 than the fragile portion 196 in particular. The wall 144 is provided between the tube 55 and the raising base 62 by the arm 206 in the same manner as described in the foregoing first embodiment. The wall 144 is formed to continuous with the fragile portion 196.

As described above, when the cover 14 is removed from the distal-end portion 32 of the insertion portion 22, the right-side edge portion 162 of the opening edge 156 is separated from the left-side edge portion 168 to break the fragile portion 196. At this time, the arm 206 is located closer to the left-side edge portion 168 than the fragile portion 196 in the proximal-end side edge portion 170. Thus, when the fragile portion 196 is broken, the wall 144 is prevented from moving together. That is, the wall 144 can prevent a load from being applied to the tube 55 and the pulling member 54.

Therefore, the position of the wall 144 is not limited to the right-side edge portion 162 of the opening edge 156 of the first structure 142a, but may be other portions such as the proximal-end side edge portion 170.

Fifth Modification

A fifth modification to the distal-end cover 14 will be described below with reference to FIGS. 16A and 16B.

The distal-end cover 14 shown in FIGS. 16A and 16B is an example in which the first and second structures 142a and 142b are integrated as one component. In other words, the cover 14 need not necessarily be configured by combining a plurality of members. As described above, the cover 14 may be formed of one member or a plurality of members such as two members.

Note that FIG. 16A shows an example in which the slit 196b is replaced with a thin portion that is thinner than its adjacent portion. Thus, the fragile portion (a region to be broken) 196 is formed in various states, such as a slit, perforations and a thin portion in such a manner that it is prevented from being broken during the use of the endoscope 10 and it is broken easily after the use, or immediately before cleaning, disinfection, sterilization, etc.

Sixth Modification

A sixth modification to the distal-end cover 14 will be described below with reference to FIG. 17.

Figure 17:
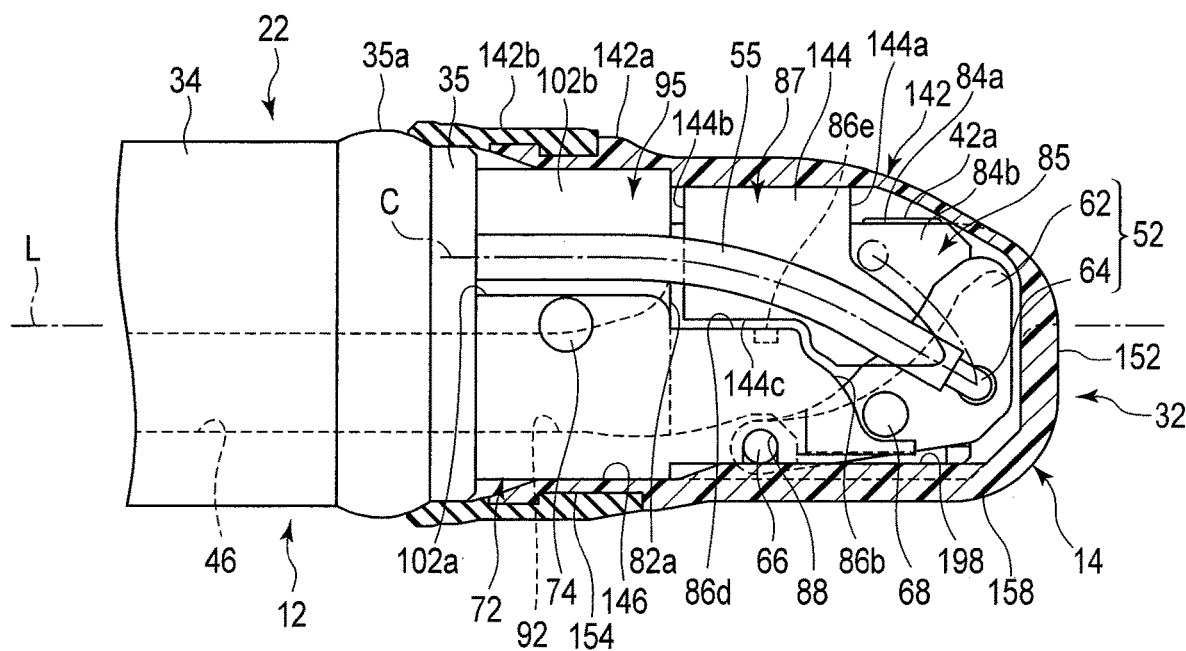
FIG. 17 is a schematic sectional view showing a state of the tube inside which the raising portion and the pulling member for operating the raising portion are disposed with respect to the wall of a distal-end cover according to a sixth modification to the first embodiment when the distal-end cover is attached to the distal-end portion of the insertion portion of the endoscope main body and the raising portion is disposed in the lowered position.

In the distal-end cover 14 shown in FIG. 17, the wall 144 differs from the above-described example in its shape. The distal end of the wall 144 is located close to the coupling portion 64 of the raising portion 52 in the lowered position. That is, it is also preferable that the wall 144 be disposed not only in the space 87 but also in the space 85 to prevent interference between the tube 55 and the raising base 62, provided that the wall 144 does not interfere with the raising portion 52.

As described above, the wall 144 is set appropriately as long as its shape does not interfere with the operation of the coupling portion 64 of the raising portion 52. For example, the wall 144 can be configured such that its edge portion 144c extends from the opening edge 156 of the cover 14 toward the extension surface 86d of the second convex portion 86 and is in contact with or close to the extension surface 86d. The wall 144 may be formed at a position where a treatment instrument tends to protrude from the guide path 62a of the raising base 62. Therefore, the size and shape of the wall 144 are set appropriately.

Seventh Modification

A seventh modification to the distal-end cover 14 will be described below with reference to FIG. 18.

Figure 18:
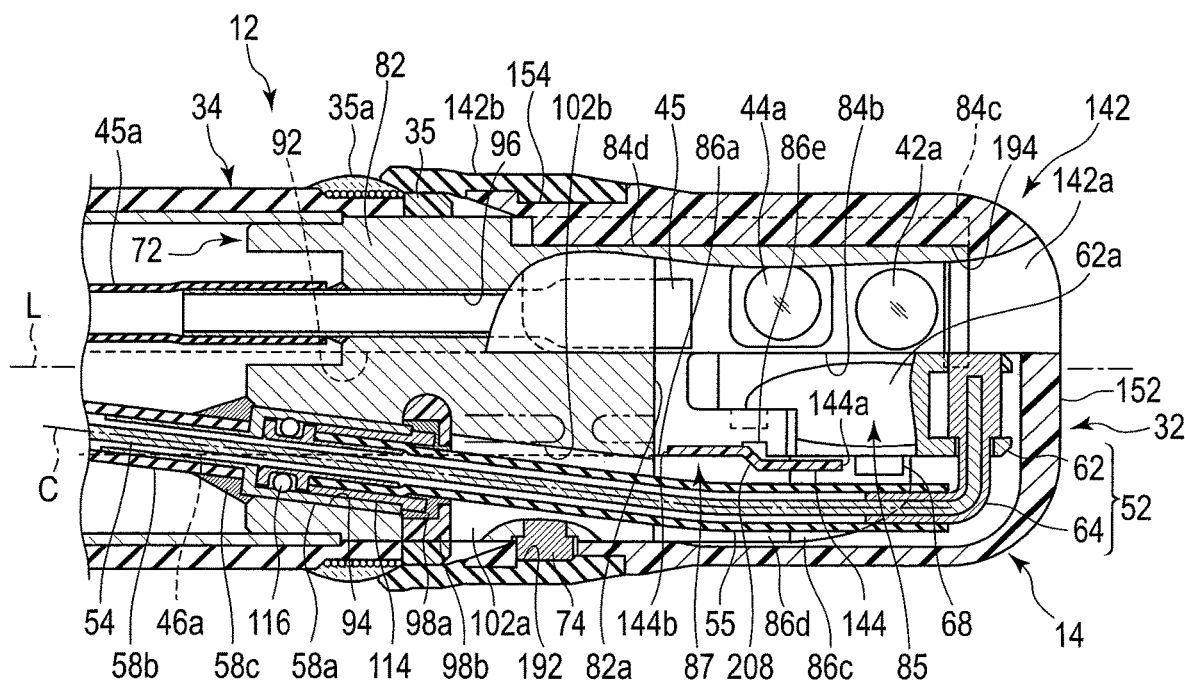
FIG. 18 is a schematic partial sectional view showing a state in which a distal-end cover having a displacement portion on a wall thereof is attached to the distal-end portion of the insertion portion of the endoscope main body according to a seventh modification to the first embodiment.

In the distal-end cover 14 shown in FIG. 18, the shape of the wall 144 differs from the example described above. The wall 144 is not planar. The proximal end 144b of the wall 144 is located close to the distal end 82a of the base portion 82 and above the proximal-end side portion of the raising base 62. As shown in FIG. 18, a portion of the wall 144, which is closer to its proximal-end side than a displacement portion 208, is disposed on the space 85 (see FIGS. 3A to 4B) in which the raising base 62 is disposed. Instead of the displacement portion 208 of the wall 144, the distal-end side of the wall 144 formed as a curved surface may be disposed on the space 85 in which the raising base 62 is disposed. It is thus possible to avoid as much as possible the contact between the portion of the wall 144 closer to the proximal-end side than the displacement portion 208 and the distal-end side portion 112a of the tube 55 where creases are formed by raising the raising base 62.

Figure 19:
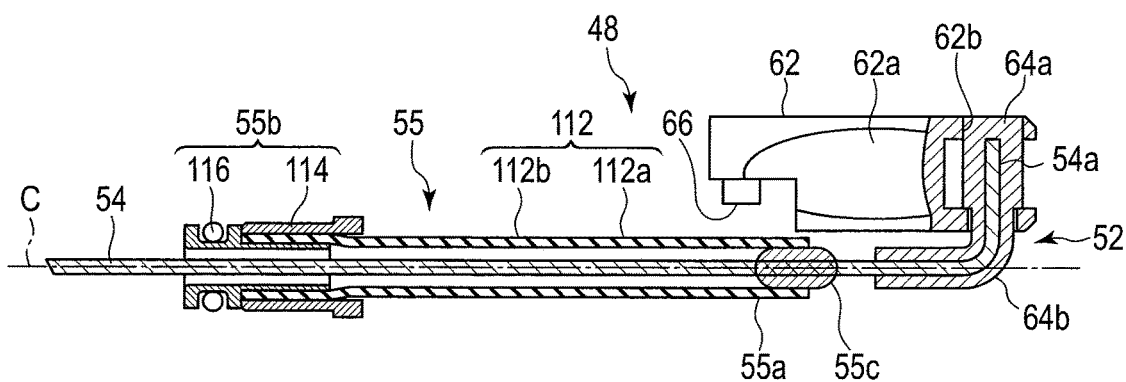
FIG. 19 is a schematic view showing a modification to the partial section of the raising portion of the raising mechanism attached to the endoscope main body of the endoscope according to the first and second embodiments including the modifications, and a modification to the section of the tube and the pulling member of the raising mechanism.
Figure 20A:
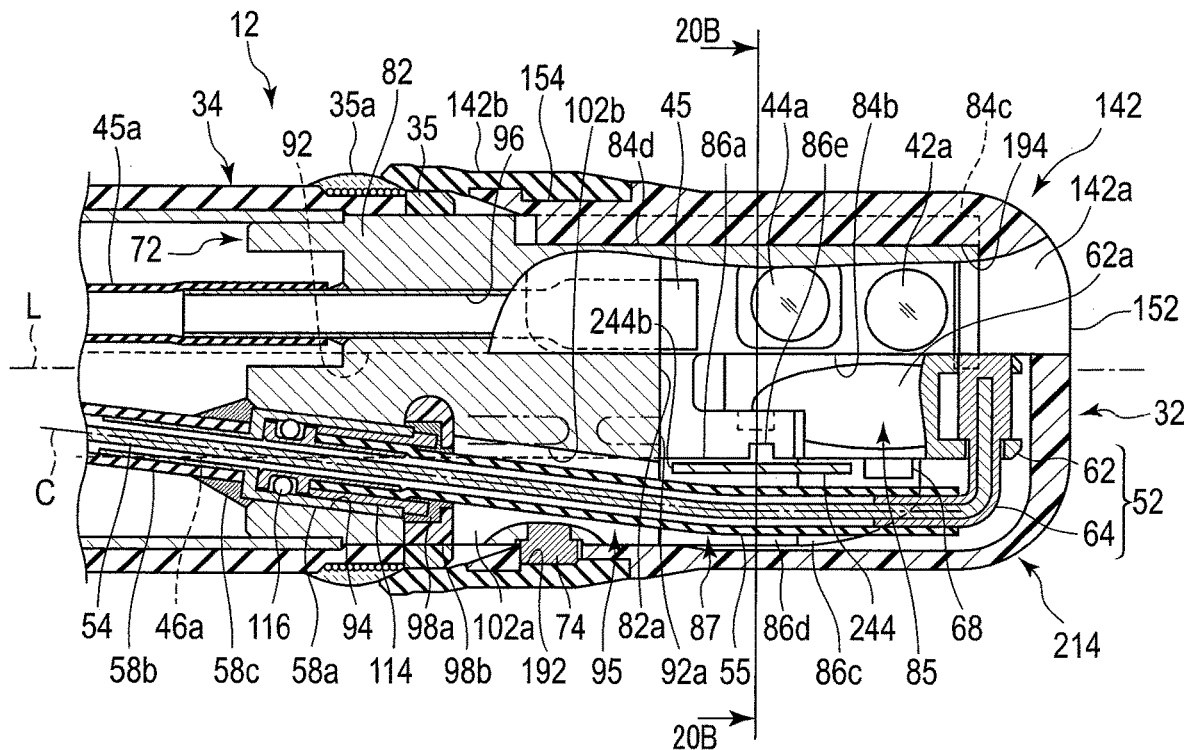
FIG. 20A is a schematic partial sectional view of an endoscope with a distal-end cover attached to an endoscope main body according to the second embodiment, showing a state in which a wall is formed on a distal frame portion of a distal-end portion of an insertion portion of the endoscope main body and a raising base is disposed in a lowered position.
Figure 20B:
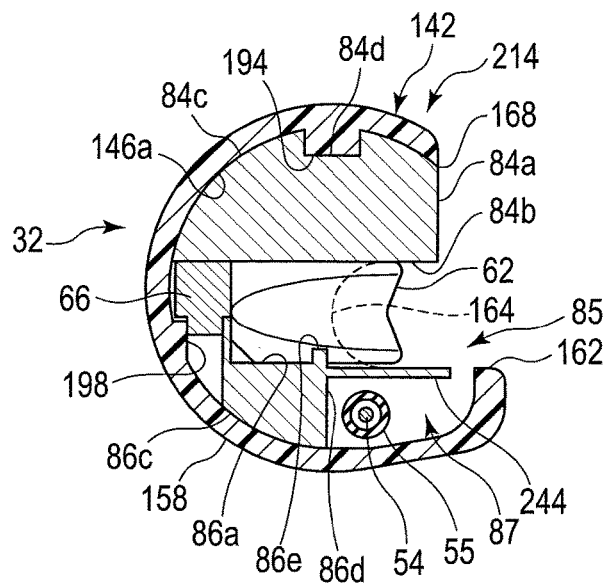
FIG. 20B is a schematic sectional view taken along line 20B-20B in FIG. 20A.

In the foregoing first embodiment including the modifications, an example in which the distal end 55a of the tube 55 is connected to the raising portion 52 has been described. As shown in FIG. 19, it is also preferable that the distal end 55a of the tube 55 is connected to the pulling member 54 watertightly by an adhesive or the like indicated by reference symbol 55c. Thus, at least part of the pulling member 54 may be exposed to the outside.

Second Embodiment

A second embodiment will be described with reference to FIGS. 20A to 21B. This embodiment is a modification of the first embodiment including the above modifications. The same reference numerals denote the same members or members having the same functions as those described in the first embodiment when possible, and a detailed description of the members will be omitted.

In the present embodiment, as shown in FIGS. 20A to 21B, a wall 244 is formed in the distal frame portion 72 of the endoscope main body 12. The wall 244 is preferably formed integrally with the distal frame portion 72 as one component by the same material (e.g. stainless steel), but may be formed of another member and fixed to the distal frame portion 72. For this reason, the distal-end cover 214 of the endoscope 10 according to the present embodiment need not be provided with the wall 144 (see FIGS. 7B and 10C) as shown in FIG. 20B. The distal-end cover 214 corresponds to the distal-end cover 14 shown in, for example, FIGS. 7B and 10 C and excluding the wall 144.

The wall 244 is provided on the distal frame portion 72 closer to the distal-end side along the longitudinal axis L than the distal-end opening 92a of the first cylindrical surface (first opening edge portion) 92. The wall 244 is formed on, for example, the extension surface 86d of the second convex portion 86 of the distal frame portion 72. The wall 244 extends from the extension surface 86d of the second convex portion 86 toward the space 87. Thus, the wall 244 extends toward the opening edge portion 156 of the cover 214.

Figure 21A:
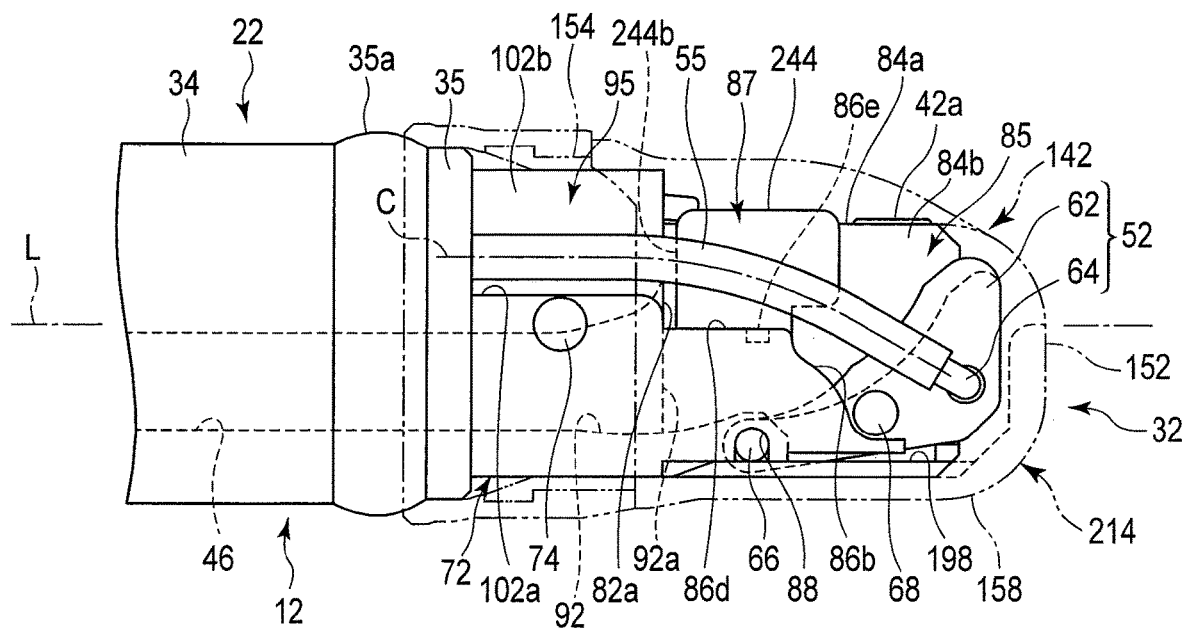
FIG. 21A is a schematic view showing a state of the tube inside which the raising portion and the pulling member for operating the raising portion are disposed with respect to the wall when the raising portion of the distal-end portion of the insertion portion of the endoscope main body according to the second embodiment is disposed in the lowered position.
Figure 21B:
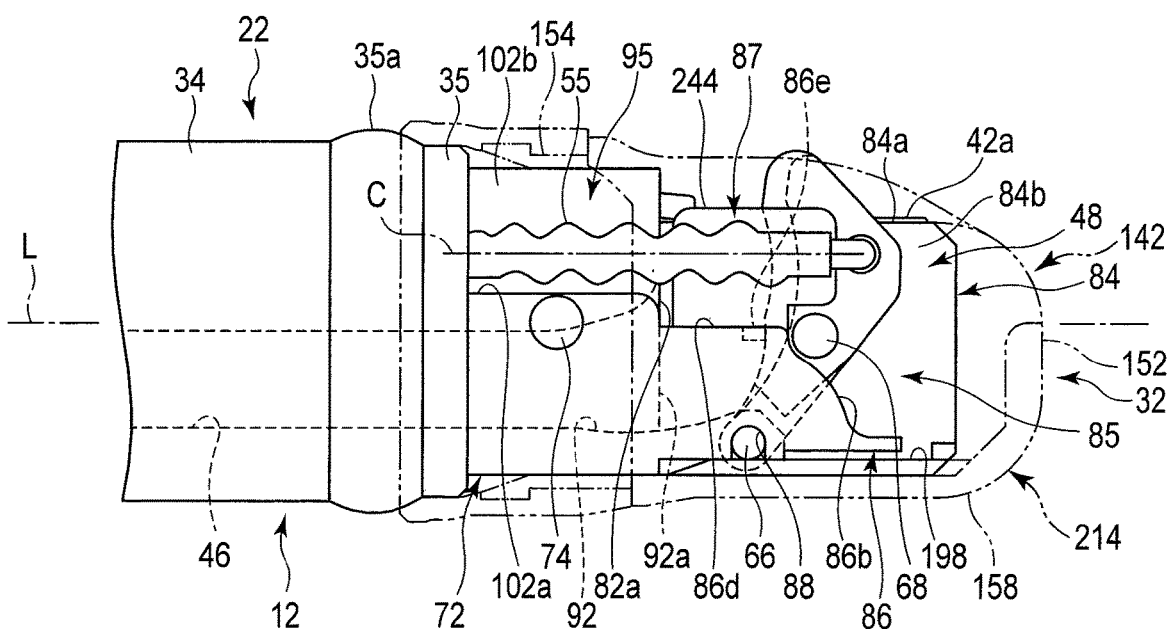
FIG. 21B is a schematic view showing a state of the tube inside which the raising portion and the pulling member for operating the raising portion are disposed with respect to the wall when the raising portion of the distal-end portion of the insertion portion of the endoscope main body according to the second embodiment is disposed in the raised position.

Like the wall 144 of the distal-end cover 14 described in the first embodiment, the wall 244 is provided between the tube 55 and the raising portion 52. As shown in FIG. 21B, the distal end of the wall 244 along the longitudinal axis L is located in a position where it does not contact the coupling portion 64 of the raising portion 52, when the raising base 62 is placed in the raised position.

As shown in FIGS. 20A to 21B, the side of the wall 244 facing the raising base 62 is preferably formed as a plane parallel to the defining surface (plane) 84b that defines the moving direction of the raising base 62. The side of the wall 244 facing the tube 55 and the pulling member 54 preferably has a surface parallel to the defining surface 84b. The side of the wall 244 facing the tube 55 and the pulling member 54 may be convex to project toward the tube 55 and the pulling member 54 and may be concave to allow deformation of the tube 55 and the pulling member 54. It is preferable that a surface of the wall 244 that is in contact with or close to the tube 55 is formed by, for example, fluorine coating so as to improve slidability with respect to the tube 55.

The following can be said about the endoscope 10 according to the present embodiment.

The wall 244 is formed in the distal frame portion 72 of the endoscope 10 between the raising portion 52 and the tube 55 inside which the pulling member 54 is disposed. According to the present embodiment, therefore, even though the raising portion 52 is operated in accordance with the movement of the pulling member 54, it is possible to provide the endoscope 10 capable of preventing the tube 55 outside the pulling member 54 from coming into contact with the raising portion 52. According to the present embodiment, furthermore, even though a treatment instrument is moved along with the operation of the raising portion 52, it is possible to provide the endoscope 10 and the distal-end cover 2 for the endoscope 10 capable of preventing the tube 55 outside the pulling member 54 from coming into contact with the raising portion 52 and the treatment instrument.

The tube 55 in FIG. 21B is formed into a wave shape when it is compressed along the central axis C, unlike the tubes shown in FIGS. 10B, 4A and 4B when the raising base 62 is located in the raised position. In this case, the deformation amount is smaller than that using the elastic member 112 described in the first embodiment as the tube 55. Since the wall 244 is disposed between the tube 55 and the raising base 62 when the raising portion 52 is raised, the deformed portion of the tube 55 can be prevented from coming into contact with the raising base 62.

As the tube 55, the elastic member 112 described in the first embodiment may be used. Since, in this case, the wall 244 is disposed between the raising base 62 and the distal-end side portion 112a of the tube 55 when the raising portion 52 is raised, the deformed distal-end side portion 112a of the tube 55 can be prevented from coming into contact with the raising base 62.

First Modification

A first modification to the endoscope 10 will be described below with reference to FIG. 22.

Figure 22:
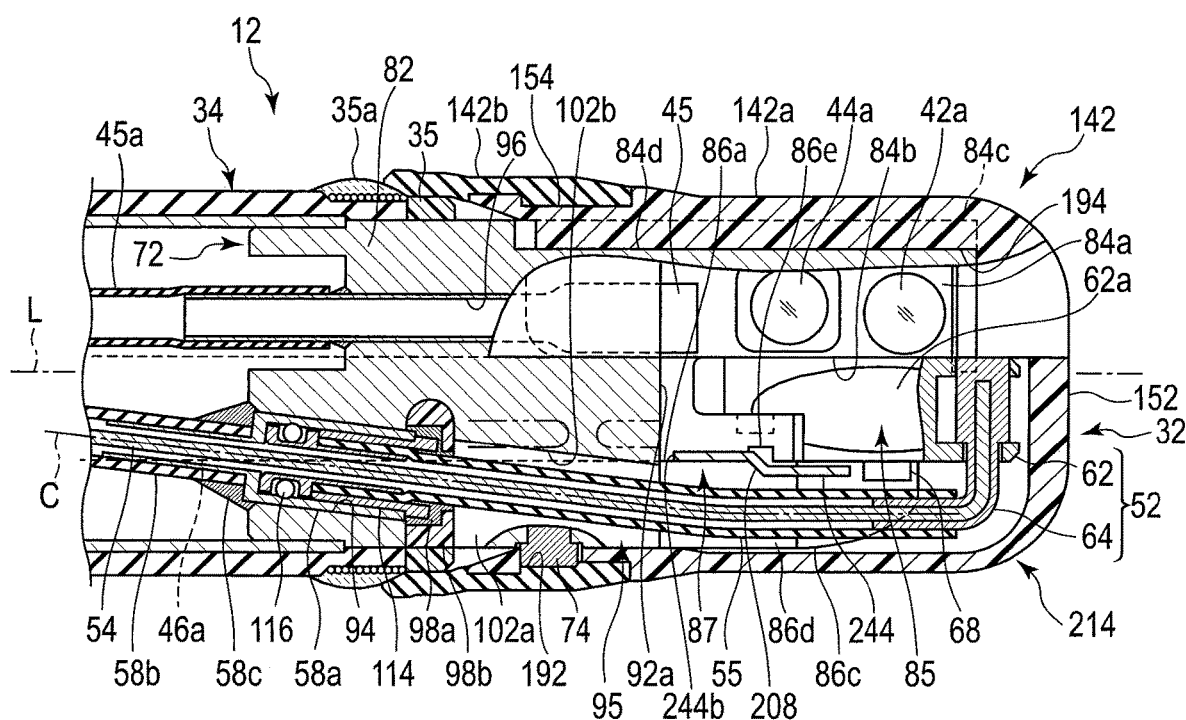
FIG. 22 is a schematic partial sectional view of an endoscope with a distal-end cover attached to an endoscope main body according to a first modification to the second embodiment, showing a state in which a wall is formed on a distal frame portion of a distal-end portion of an insertion portion of the endoscope main body and a raising base is disposed in a lowered position.

The shape of the wall 244 provided in the distal frame portion 72 shown in FIG. 22 differs from the example described above. The wall 244 is not planar. The proximal end 244b of the wall 244 is located close to the distal end 82a of the base portion 82 and above the proximal-end side portion of the raising base 62. As shown in FIG. 22, a portion of the wall 244, which is closer to its proximal-end side than the displacement portion 208, is disposed on the space 85 (see FIGS. 3A to 4B) in which the raising base 62 is disposed. Note that the distal-end side of the wall 244 formed as a curved surface may be disposed on the space 85 in which the raising base 62 is disposed. If the elastic member 112 is used as the tube 55, creases are formed in the distal-end side portion 112a of the tube 55 when the raising base 62 is located in the raised position. Even in this case, it is possible to avoid as much as possible the contact between the portion of the wall 244 closer to the proximal-end side than the displacement portion 208 and the distal-end side portion 112a of the tube 55 where the creases are formed by raising the raising base 62.

Second Modification

A second modification to the endoscope 10 will be described below with reference to FIGS. 23A to 26B.

Here is a description of an example where a wall 344 is formed in the distal frame portion 72 of the endoscope main body 12 as shown in FIGS. 23A to 24B. As shown in FIGS. 23B and 24A, the wall 144 (see FIGS. 7A to 7C) need not be formed in the distal-end cover 214.

Figure 23A:
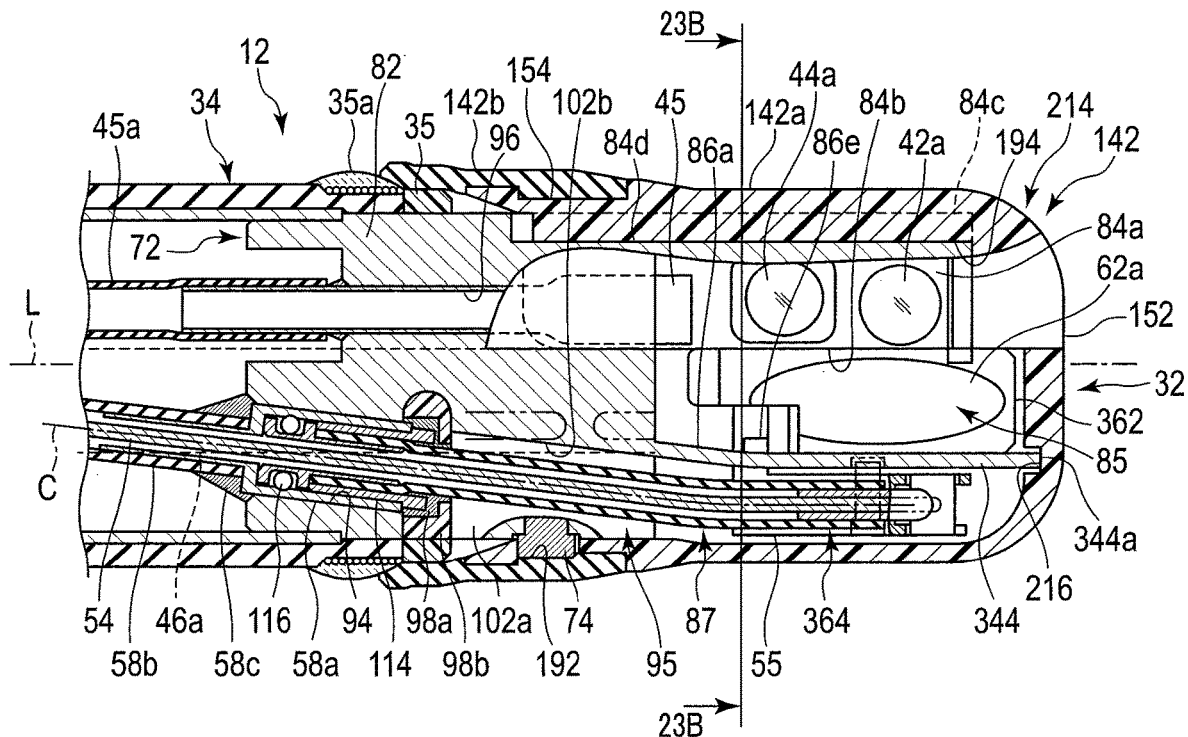
FIG. 23A is a schematic partial sectional view of an endoscope with a distal-end cover attached to an endoscope main body according to a second modification to the second embodiment, showing a state in which a wall is formed on a distal frame portion of a distal-end portion of an insertion portion of the endoscope main body and a raising base is disposed in a lowered position.

As shown in FIG. 23A, the wall 344 extends toward the distal-end side along the longitudinal axis L to continue to, for example, the second wall surface (side surface) 102b of the base portion 82 of the distal frame portion 72. That is, the wall 344 is formed of the same material (e.g. stainless steel) as the distal frame portion 72 and extends toward the distal-end side along the longitudinal axis L from the distal end 82a of the base portion 82 of the distal frame portion 72. The wall 344 is provided to separate the space 85 in which the raising base 62 of the raising portion 52 is disposed and the space 87 in which the pulling member 54 and the tube 55 are disposed. It is preferable that a surface of the wall 344 that is in contact with or close to the tube 55 is formed by, for example, fluorine coating so as to improve slidability of the tube 55 with respect to the wall 344.

Figure 23B:
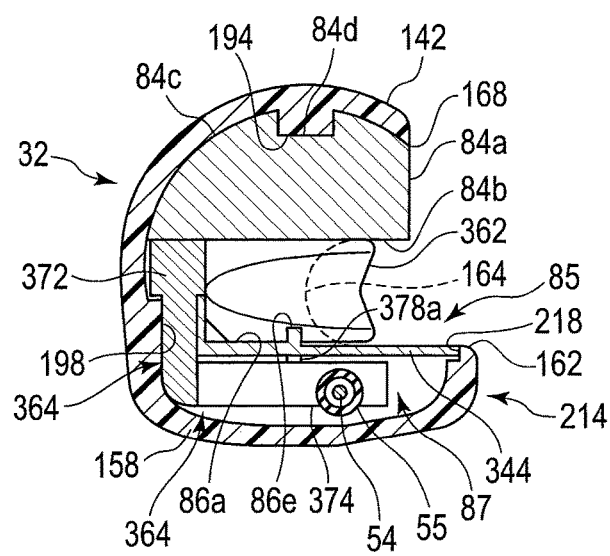
FIG. 23B is a schematic sectional view taken along line 23B-23B in FIG. 23A.
Figure 24A:
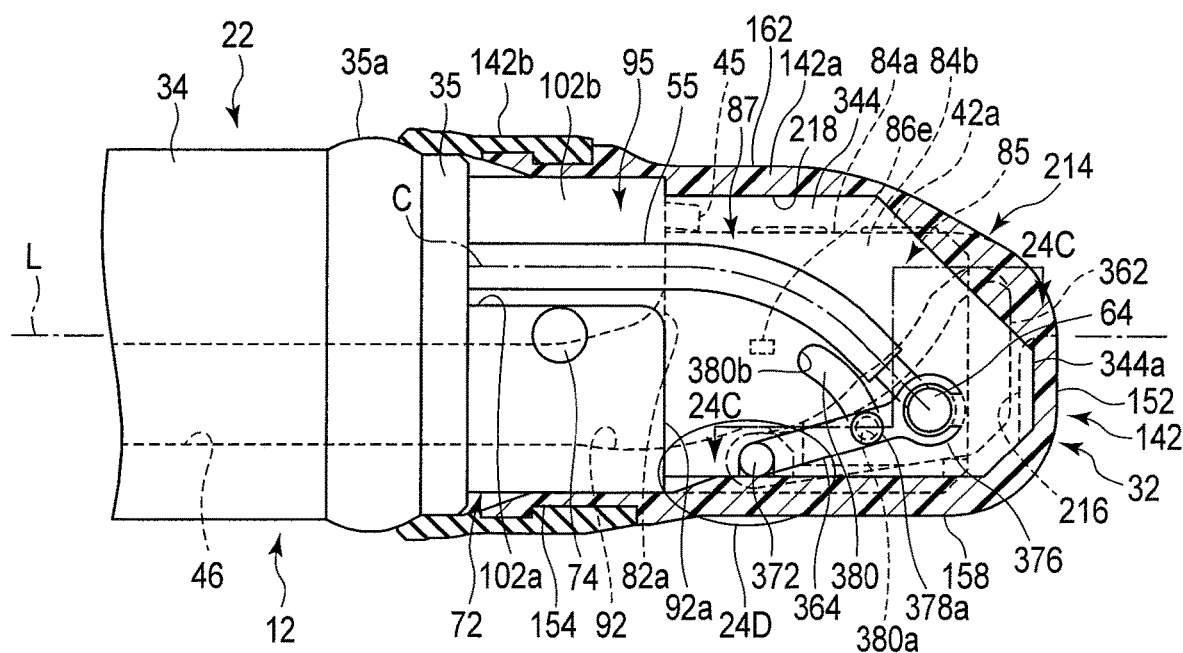
FIG. 24A is a schematic partial sectional view showing a state of the tube inside which the raising portion and the pulling member for operating the raising portion are disposed with respect to the wall of the distal frame portion when the distal-end cover is attached to a distal-end portion of the insertion portion of the endoscope main body and the raising portion is disposed in the lowered position.

A distal-end side fitting receiving portion 216 is formed on the inner circumferential surface of the closing portion 152 of the distal-end cover 214. The distal end 344a of the wall 344 is fit to the distal-end side fitting receiving portion 216 of the distal-end cover 214. As shown in FIG. 23B, a right-side fitting receiving portion 218 is formed on the right-side edge portion 162 of the distal-end cover 214. Preferably, the right-side fitting receiving portion 218 is continuous with the distal-end side fitting receiving portion 218. As shown in FIG. 24A, in the edge portion of the wall 344, not only the distal end 344a but also a portion close to the opening edge 156 is preferably supported by the cover 214.

Figure 25:
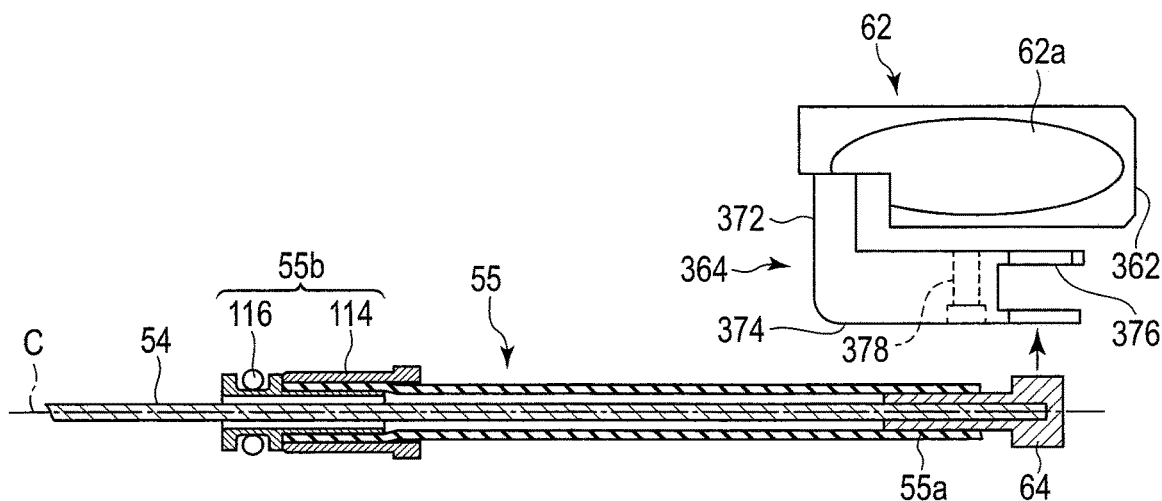
FIG. 25 is a partial sectional view showing the raising portion of the raising mechanism, the pulling member to the distal end of which a coupling portion is coupled, and the tube inside which the pulling member is disposed in the second modification to the second embodiment.

As shown in FIG. 25, the raising portion 52 includes a raising base 62 having a guide path 62a for treatment instruments and a coupling portion 64 coupled to the raising base 62.

The raising base 62 includes a raising base main body 362 with the guide path 62a and a substantially L-shaped fitting arm 364 extending from the main body. The fitting arm 364 includes a pivot shaft 372 orthogonal to the longitudinal axis L and orthogonal to the observation direction from the proximal end of the raising base main body 362 and an arm portion 374 orthogonal to the pivot shaft 372. The pivot shaft 372 is provided on the raising base main body 362. A pivot shaft 372 is integrated with the proximal end of the arm portion 374. The pivot shaft 372 is shaped like a circular rod pivotally supported by a support portion 382 (described later) of the wall 344. A support portion 376 is provided at the distal end of the arm portion 374 to support the coupling portion 64. Between the proximal end (pivot shaft 372) and the distal end (support portion 376) of the arm portion 374, a through hole 378 is formed to penetrate in a direction orthogonal to the longitudinal axis L and orthogonal to the observation direction.

As shown in FIGS. 24A to 24C and 26A, a concave groove 380 is formed in the back surface of a surface of the wall 344, which is opposed to the defining surface 84b of the first convex portion 84. As shown in FIGS. 24A, 24B, 24D and 26A, a support portion 382 that supports the pivot shaft 372 as a pivot center is formed at an edge portion on the side opposite to a position where the right-side fitting receiving portion 218 of the right-side edge portion 162 of the cover 214. The support portion 382 is formed in a substantially U-shape. The concave groove 380 is provided in a position in which an arc is drawn about the pivot shaft 372 of the fitting arm 364 supported by the support portion 382.

As shown in FIGS. 23A to 24D, the raising base main body 362 is disposed in the space 85 and the pivot shaft 372 is disposed in the support portion 382. The arm portion 374 is disposed in the space 87. A pin 378a is disposed in the through hole 378. The pin 378a is provided in parallel with the pivot shaft 372 at a position separated from the pivot shaft 372. One end of the pin 378a is in contact with the concave groove 380. Therefore, even though the cover 214 is not provided at the distal-end portion 32, the pivot shaft 372 of the raising base 62 is prevented from slipping off the support portion 382 of the wall 344. In other words, when one end of the pin 378a is disposed in the concave groove 380, the concave groove 380 and pin 378a maintain a state in which the pivot shaft 372 of the fitting arm 364 is supported by the support portion 382.

Figure 24B:
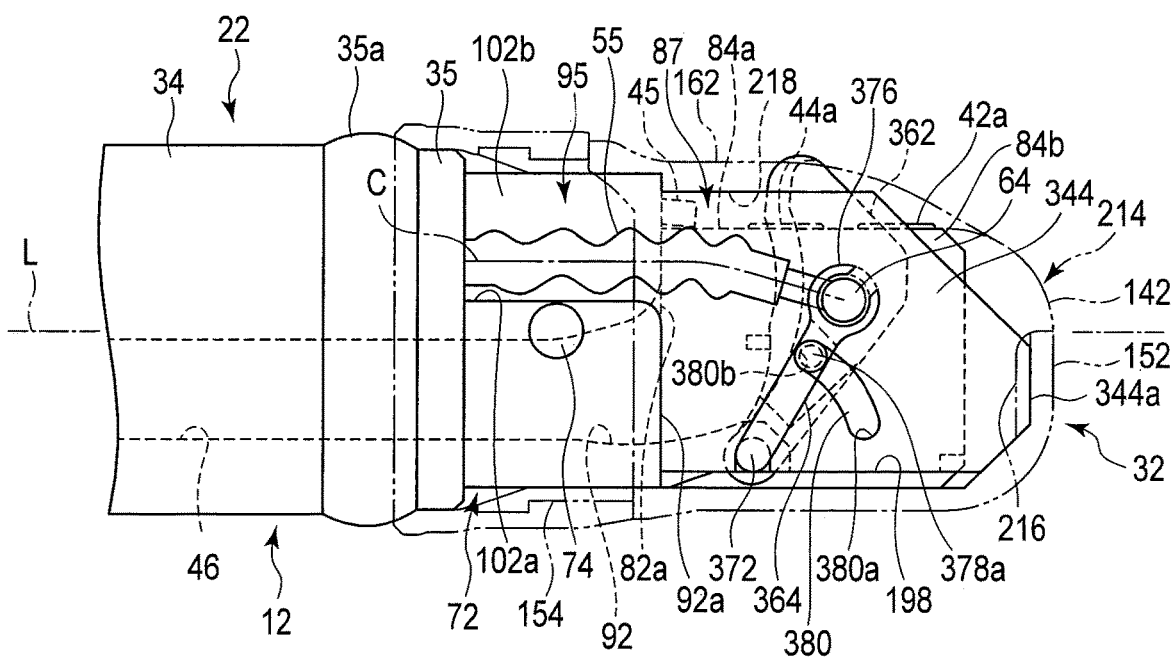
FIG. 24B is a schematic view showing a state of the tube inside which the raising portion and the pulling member for operating the raising portion are disposed with respect to the wall of the distal frame portion when the raising portion is disposed in the raised position.
Figure 24C:
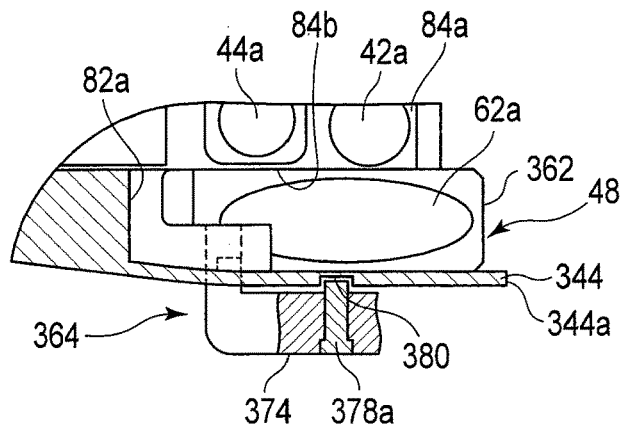
FIG. 24C is a schematic sectional view taken along line 23C-23C in FIG. 24A.

As shown in FIG. 24A, when the raising base 62 is in the lowered position, one end of the pin 378a is close to or in contact with one end 380a of the concave groove 380. As shown in FIG. 24B, when the raising base 62 is in the raised position, one end of the pin 378a is close to or in contact with the other end 380b of the concave groove 380.

Figure 24D:
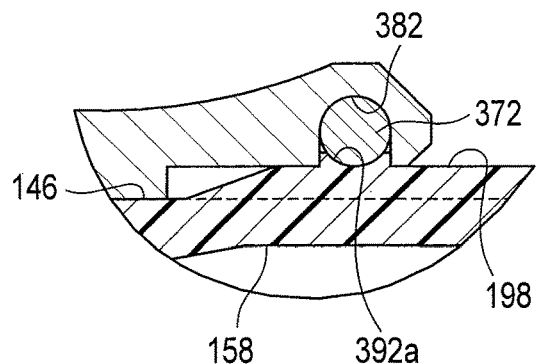
FIG. 24D is a schematic partial sectional view showing a relationship between the fitting arm and the raising base main body of the raising mechanism with respect to the wall in the enlarged position indicated by symbol 24D in FIG. 24A.
Figure 26A:
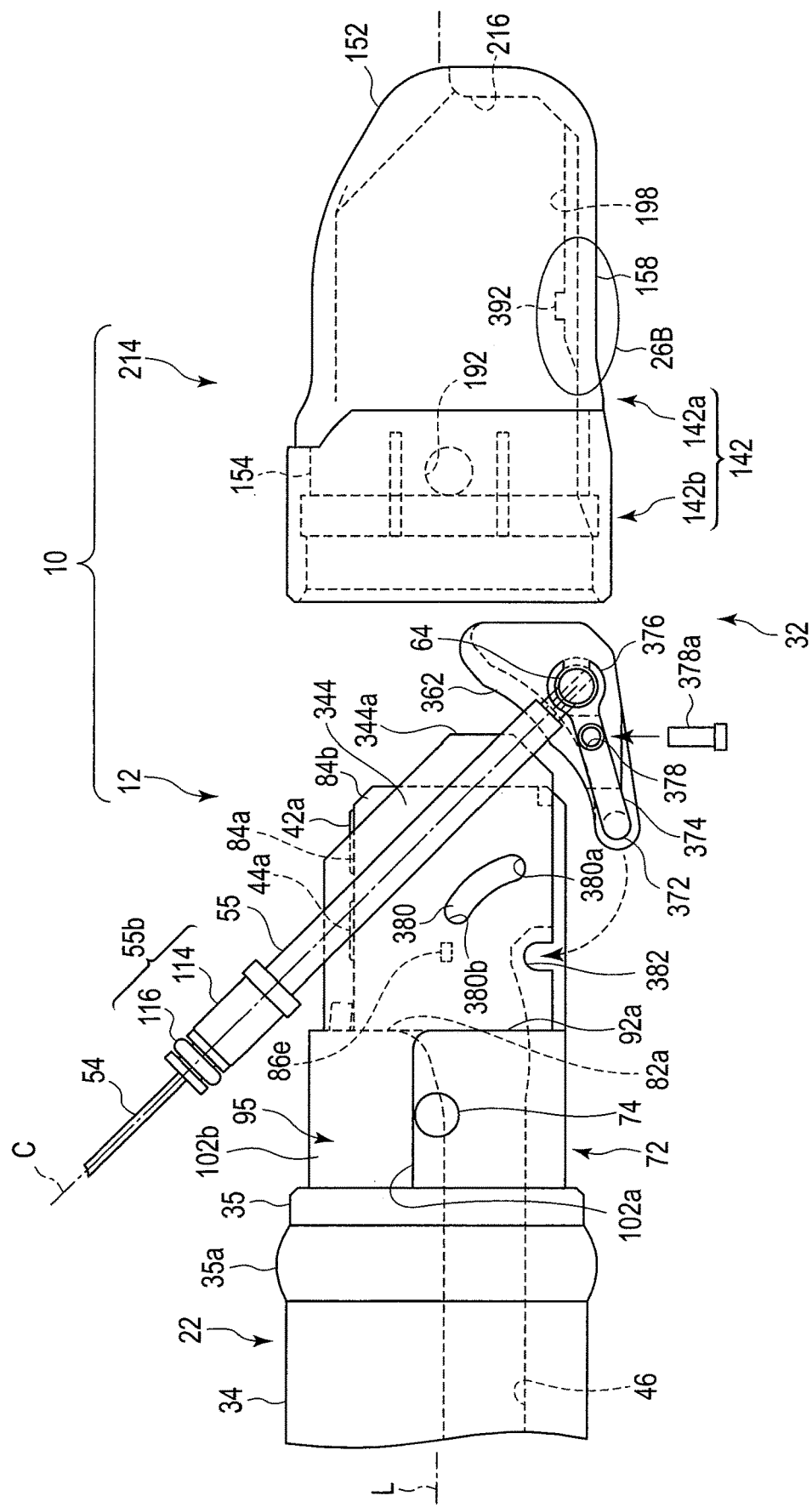
FIG. 26A is a schematic view showing a state in which the raising mechanism is attached to the distal frame portion of the insertion portion of the endoscope main body according to the second modification to the second embodiment, which is provided with a wall, and then the distal-end cover is going to be attached thereto.

A cover 214 is attached to the outside of the distal-end portion 32. As shown in FIGS. 26A and 26B, a convex portion 392 having an arc-shaped concave portion 392a is formed on the convex portion 198 of the inner circumferential surface 146 of the cover 214. As shown in FIG. 24D, the concave portion 392a supports the pivot shaft 372. At this time, the concave portion 392a supports the pivot shaft 372 in a substantially annular manner in cooperation with the support portion 382. For this reason, the concave portion 392a of the cover 214, the pivot shaft 372 of the raising base 62 and the support portion 382 of the wall 344 minimizes a gap in which a liquid moves from the raising base main body 362 to the arm portion 374 through the pivot shaft 372 to suppress the movement of the liquid. Therefore, the movement of a body fluid or the like from the space 85 to the space 87 is suppressed as much as possible.

Note that the concave portion 392a of the convex portion 392 may be fit to the pivot shaft 66 and the support portion 88 described in the first embodiment. In this case, the movement of liquid or the like from the raising base 62 toward the outer circumferential surface 86c of the second convex portion 86 is suppressed as much as possible.

As shown in FIGS. 23A to 24B, the distal end 344a of the wall 344 is made close to or placed into contact with the inner circumferential surface of the cover 214 with the cover 214 properly attached to the distal-end portion 32. In addition, the wall 344 is made close to or placed into contact with the right-side edge portion 162 of the opening edge 156 of the first structure 142a of the cover 214. In this case, it becomes difficult for contaminants and the like to enter the space in which the tube 55 and the pulling member 54 are disposed. After the endoscope 10 is used, the possibility that contaminants adhere to the vicinity of the tube 55 of the distal-end portion 32 of the endoscope main body 12 is decreased. Thus, there is a high possibility that it need not be cleaned more carefully than in the above-described example. The cleaning time can thus be shortened.

Note that the cover 214 according to the second embodiment has been described as not having the wall 144. Of course, as in the cover 314 shown in FIG. 27, a single wall can be formed by cooperating the wall 144 of the cover 14 according to the first embodiment and the wall 344 of the distal frame portion 72 according to the second embodiment with each other. In this case, in accordance with the relationship between the wall 344 and the distal-end cover 314, one of the structure of the raising portion 52 described in the first embodiment and the structure of the raising portion 52 described in the second modification to the second embodiment can be selected and used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A distal-end cover for use with an endoscope, the distal-end cover comprising:
    a cover main body configured to be attached to a distal-end side of an insertion portion of an endoscope main body, the endoscope main body comprising:
        a distal frame portion provided on the distal-end side of the insertion portion along the longitudinal axis, the distal frame portion comprising:
            a first opening forming part of a channel through which a treatment instrument is inserted, and
            a second opening provided separately from the first opening;
        a raising lever rotatably attached to the distal frame portion, and the raising lever being configured to raise the treatment instrument to protrude from the first opening;
        an elongated member inserted through the second opening, the elongated member being connected to the raising lever and configured to be moved along the longitudinal axis of the insertion portion to rotate the raising lever; and
        a tube inside which the elongated member is disposed, one end of the tube being watertightly connected to one of the raising lever and the elongated member, and the other end of the tube being watertightly connected to the second opening; and
    a wall provided on the cover main body,
    the wall being provided between the tube and the raising lever closer to the distal-end side along the longitudinal axis than the first opening when the cover main body is attached to an outside of the distal frame portion along the longitudinal axis of the insertion portion, and
    the wall being deformed by the tube and the elongated member when the cover main body is removed from the outside of the distal frame portion.

2. The distal-end cover of claim 1, wherein:
    the cover main body has a cylindrical shape and includes a proximal-end opening and an opening edge through which the treatment instrument is inserted, and
    the wall is provided on the opening edge.

3. The distal-end cover of claim 2, wherein:
    the wall is formed separately from the cover main body, and
    the wall is fixed to the opening edge.

4. The distal-end cover of claim 2, wherein the wall extends from the opening edge toward an inner circumferential surface of the cover main body opposed to the opening edge.

5. The distal-end cover of claim 1, wherein the wall is formed integrally with the cover main body.

6. The distal-end cover of claim 1, wherein the wall includes a fragile portion which is bent by pressure received from the tube when the cover main body is removed from the endoscope main body.

7. The distal-end cover of claim 1, wherein the cover main body comprises:
    a cylindrical first structure comprising:
        a proximal-end opening, and
        an opening edge through which the treatment instrument is inserted, the first structure being disposed outside the distal frame portion, and the first structure protecting the distal frame portion, the raising lever, the elongated portion and the tube,
    a cylindrical second structure which holds an outer circumference of the proximal-end opening with the opening edge exposed; and the wall is formed integrally with the second structure and extends from the opening edge toward the first structure opposed to the opening edge.

8. An endoscope comprising:
an endoscope main body comprising:
an insertion portion elongated along a longitudinal axis, the insertion portion being configured to be inserted into a subject;
a distal frame portion provided on a distal-end side of the insertion portion along the longitudinal axis, the distal frame portion comprising:
a first opening forming part of a channel through which a treatment instrument is inserted, and
a second opening provided separately from the first opening;
a raising lever rotatably attached to the distal frame portion, the raising lever being configured to raise the treatment instrument to protrude from the first opening;
an elongated member inserted through the second opening, the elongated member being connected to the raising lever and configured to be moved along the longitudinal axis of the insertion portion to rotate the raising lever; and
a tube inside which the elongated member is disposed, one end of the tube being watertightly connected to one of the raising lever and the elongated member, and the other end of the tube being watertightly connected to the second opening; and
a distal-end cover comprising:
a cover main body configured to be attached to a distal-end side of an insertion portion of an endoscope main body; and
a wall provided on the cover main body,
the wall being provided between the tube and the raising lever closer to the distal-end side along the longitudinal axis than the first opening when the cover main body is attached to an outside of the distal frame portion along the longitudinal axis of the insertion portion, and
the wall being deformed by the tube and the elongated member when the cover main body is removed from the outside of the distal frame portion.

9. The endoscope of claim 8, wherein:
the tube is provided such that creases are formed therein as the elongated member moves; and
the wall separates a portion of the tube where the creases are formed from the raising lever between the tube and the raising lever.

10. The endoscope of claim 9, wherein the creases of the tube are easily formed at a position closer to the one end of the tube than the other end thereof.

11. The endoscope of claim 8, wherein a distal-end opening of the first opening is closer to the distal-end side along the longitudinal axis than a distal-end opening of the second opening, in the distal frame portion.

12. The endoscope of claim 8, wherein:
the raising lever is rotatable about a pivot shaft with respect to the distal frame portion;
the pivot shaft is positioned on the inner circumferential surface of the distal-end cover with respect to the distal frame portion, the wall is provided between the tube and the raising lever when the cover main body is attached to the outside of the distal frame portion; and
the positioning of the pivot shaft with respect to the distal frame portion is released as the cover main body is removed from outside the distal frame portion and the wall is moved from between the tube and the raising lever.

13. The endoscope of claim 8, wherein:
the distal frame portion includes an engaging portion which engages the cover main body with the distal frame portion when the cover main body is attached to the outside of the distal frame portion along the longitudinal axis of the insertion portion; and
the engaging portion is separated from a portion between the tube and the raising lever, in which the wall is provided.

14. A distal-end cover for use with an endoscope, the distal-end cover comprising:
a cover main body configured to be attached to a distal frame portion of an insertion portion of an endoscope main body; and
a wall provided on the cover main body,
the wall being provided between a tube and a raising lever provided on the endoscope main body, the wall being closer to the distal-end side along the longitudinal axis than a first opening of the distal frame portion forming part of a channel through which a treatment instrument is inserted when the cover main body is attached to an outside of the distal frame portion along the longitudinal axis of the insertion portion, and
the wall being deformed by the tube and an elongated member of the endoscope main body when the cover main body is removed from the outside of the distal frame portion,
where:
the elongated member is disposed inside the tube,
the elongated member is inserted through a second opening provided separately from the first opening,
the elongated member is connected to the raising lever, and is configured to be moved along the longitudinal axis of the insertion portion to rotate the raising lever,
one end of the tube is watertightly connected to one of the raising lever and the elongated member, and the other end of the tube is watertightly connected to the second opening, and
the raising lever of the endoscope main body is rotatably attached to the distal frame portion, and is configured to raise the treatment instrument to protrude from the first opening.

15. A distal-end cover for use with an endoscope, the distal-end cover comprising:
a cover main body configured to cover a distal end of the endoscope, the cover main body defining an interior configured to accommodate the distal end of the endoscope, the cover main body comprising:
an edge defining an opening, the opening having a central axis offset from a longitudinal axis of the cover main body;
a wall having a single side attached to a portion of the edge of the opening such that all other portions of the wall are cantilevered from the portion of the edge of the cover main body, all of the other portions of the wall extending from the portion of the edge into the interior of the cover main body.

16. The distal-end cover of claim 15, wherein the cover main body has a cylindrical shape and includes a proximal-end opening.

17. The distal-end cover of claim 15, wherein:
the wall is formed separately from the cover main body, and
the wall is fixed to the portion of the edge.

18. The distal-end cover of claim 15, wherein the wall extends from the edge toward an inner circumferential surface of the cover main body opposed to the opening.

19. The distal-end cover of claim 15, wherein the wall is formed integrally with the cover main body.

20. The distal-end cover of claim 15, wherein the wall includes a fragile portion connecting the wall to the portion of the edge, the fragile portion being more fragile than other portions of the wall.

* * * * *